US008242461B2

(12) United States Patent
Rösicke et al.

(10) Patent No.: US 8,242,461 B2
(45) Date of Patent: Aug. 14, 2012

(54) INTEGRATED TEST ELEMENT

(75) Inventors: Bernd Rösicke, Mannheim (DE); Kai Hebestreit, Heidelberg (DE); Claudia Gässler-Dietsche, Schriesheim (DE); Frederic Wehowski, Hockenheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 364 days.

(21) Appl. No.: 12/231,119

(22) Filed: Aug. 29, 2008

(65) Prior Publication Data

US 2009/0061076 A1 Mar. 5, 2009

Related U.S. Application Data

(63) Continuation of application No. PCT/EP2007/051799, filed on Feb. 26, 2007.

(30) Foreign Application Priority Data

Mar. 2, 2006 (EP) ...................................... 06110608

(51) Int. Cl.
*G01J 1/02* (2006.01)

(52) U.S. Cl. ............... 250/458.1; 250/459.1; 250/461.1; 422/82.01

(58) Field of Classification Search ............... 250/458.1; 257/40
See application file for complete search history.

(56) References Cited

U.S. PATENT DOCUMENTS

| 4,769,292 | A | * | 9/1988 | Tang et al. | ..................... | 428/690 |
| 4,889,690 | A | | 12/1989 | Opitz et al. | | |
| 5,157,262 | A | * | 10/1992 | Marsoner et al. | .......... | 250/458.1 |
| 6,303,943 | B1 | * | 10/2001 | Yu et al. | ........................ | 257/40 |
| 6,331,438 | B1 | | 12/2001 | Aylott et al. | | |
| 7,044,911 | B2 | * | 5/2006 | Drinan et al. | .................. | 600/300 |
| 2004/0217702 | A1 | * | 11/2004 | Garner et al. | ................. | 313/512 |
| 2004/0235185 | A1 | | 11/2004 | Horn et al. | | |
| 2006/0098203 | A1 | | 5/2006 | Kalveram | | |
| 2006/0099327 | A1 | | 5/2006 | Horn et al. | | |
| 2006/0121625 | A1 | | 6/2006 | Clemens et al. | | |

FOREIGN PATENT DOCUMENTS

DE 102 54 685 A1 3/2004

(Continued)

OTHER PUBLICATIONS

Choudhury et al., Glucose Biosensors Based on Organic Light-Emitting Devices Structurally Integrated with a Luminescent Sensing Element, Journal of Applied Physics, Sep. 1, 2004, p. 2949-2954, vol. 96, No. 5, Copyright 2004 American Institute of Physics.

(Continued)

*Primary Examiner* — Sally Sakelaris

(74) *Attorney, Agent, or Firm* — Kevin J. Huser; Krieg DeVault LLP

(57) ABSTRACT

An integrated test element (110) is proposed for detecting for detecting at least one analyte in a sample (142), in particular in a liquid sample (142). The integrated test element (110) has a carrier element (112), with an application face (114) on which at least one organic electroluminescent component (126) is applied. Furthermore, at least one indicator substance (136) is applied on the application face (114), which indicator substance (136) alters at least one optical characteristic, in particular an emission characteristic (e.g. a fluorescence characteristic), when it comes into contact with the at least one analyte. Furthermore, the integrated test element (110) has at least one photodetector element (116).

26 Claims, 6 Drawing Sheets

FOREIGN PATENT DOCUMENTS

| | | |
|---|---|---|
| DE | 102 53 154 A1 | 5/2004 |
| DE | 103 04 448 A1 | 8/2004 |
| EP | 0 244 394 A2 | 11/1987 |
| EP | 0 811 154 B1 | 4/2005 |
| NL | WO2005015173 * | 2/2005 |
| WO | WO 03/097859 A2 | 11/2003 |
| WO | WO 2005/015173 | 2/2005 |

OTHER PUBLICATIONS

Hofmann et al., Towards Microalbuminuria Determination on a Disposable Diagnostic Microchip with Integrated Fluorescence Detection Based on Thin-Film Organic Light Emitting Diodes, Lab Chip, 2005, p. 863-868, Copyright The Royal Society of Chemistry.

Wong et al., Spiro-Configured Bifluorenes: Highly Efficient Emitter for UV Organic Light-Emitting Device and Host Material for Red Electrophosphorescence, Aug. 4, 2005, 4 pages, vol. 0 No. 0, Copyright xxxx American Chemical Society.

Wong et al., Ter(9,9-diarylfluorene)s: Highly Efficient Blue Emitter with Promising Electrochemical and Thermal Stability, J. Am. Chem. Soc., 2002, p. 11576-11577, vol. 124 No. 39, Copyright 2002 American Chemical Society.

* cited by examiner

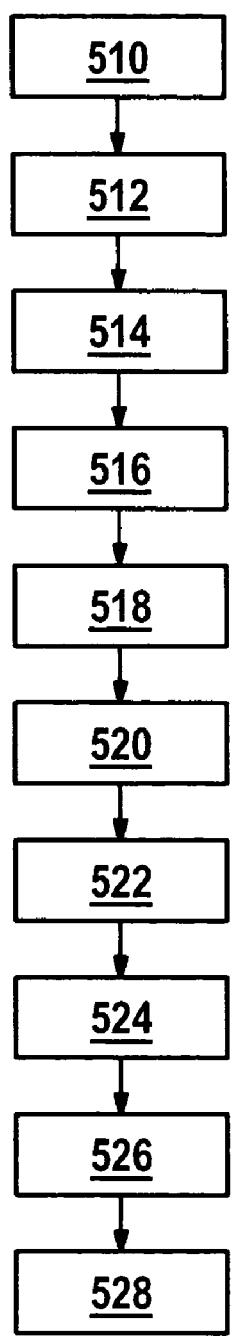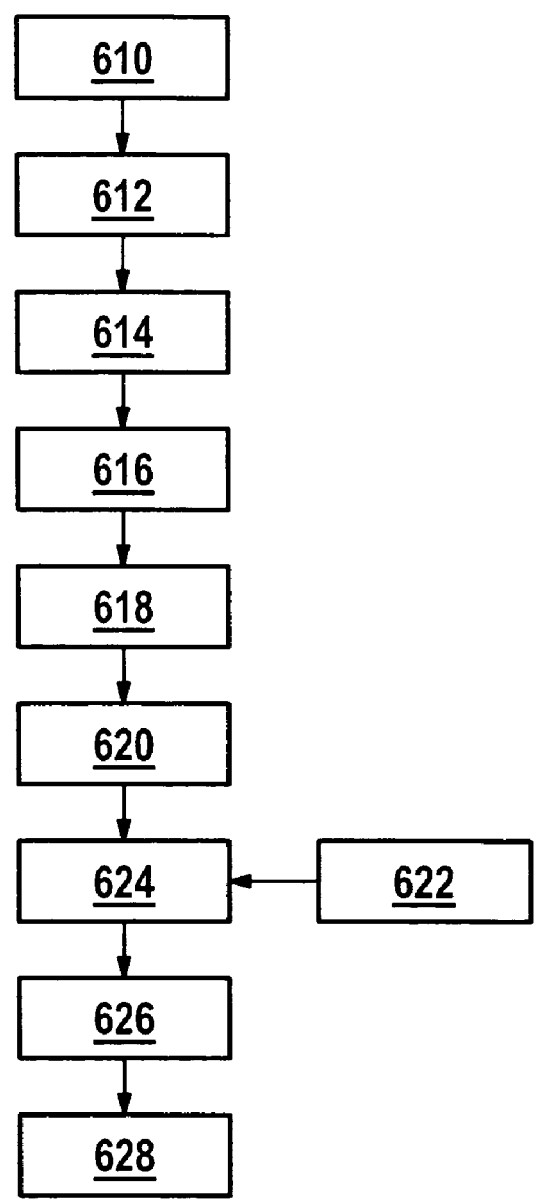

INTEGRATED TEST ELEMENT

CROSS-REFERENCE TO RELATED APPLICATIONS

This application claims the benefits under 35 U.S.C. 120 as a continuation of International Application No. PCT/EP2007/051799 filed 26 Feb. 2007, which claims priority to European Patent Application No. EP 06110608.4 filed 2 Mar. 2006. Each of the referenced applications is incorporated herein by reference in its entirety.

FIELD OF THE INVENTION

The invention relates to an integrated test element for detecting at least one analyte in a sample, in particular in a liquid sample. Such test elements are used, for example in medicine and analytical chemistry, for detection, for example rapid testing, of certain chemicals and substances, and also in biochemistry, in medical analysis, in the field of safety technology, in the field of environmental technology or in other areas of natural sciences and technology.

BACKGROUND

Rapid, simple and reliable detection of certain analytes in a sample is of crucial importance in various fields of technology and natural sciences. Numerous detection methods are employed, depending on the requirements and on the desired accuracy. A method known from the prior art, and existing in many different variations, is of an optical nature and is based on the fact that the analyte to be detected in many cases exerts an influence on the optical properties of certain indicator substances. Thus, for example, the analyte can influence a fluorescence and/or phosphorescence behavior of an indicator substance, for example by reducing (quenching) the intensity of a fluorescence light, which the indicator substance emits under excitation by an excitation light source, in the presence of the analyte to be detected. Instead of a reduction, the opposite effect can also be exploited, for example by a fluorescence behavior being increased, or even being initially generated, when the analyte interacts with the indicator substance. Many such methods are known from the prior art.

Thus, for example, in B. Choudhury et al.: Glucose biosensors based on organic light-emitting devices structurally integrated with a luminescent sensing element, Journal of Applied Physics, 96 (5), 2949, 2004, a device is described which uses an optical method for glucose detection, said method being based on enzymatic oxidation of glucose in the presence of glucose oxidase (GOD). The glucose concentration is measured by means of an oxygen-sensitive dye, which is present together with the glucose oxidase in an indicator layer or in a solution. Instead of glucose oxidase for detection of glucose, it is alternatively possible to use glucose dehydrogenase (GlucDH) as catalyst for converting glucose to gluconolactone in the presence of NAD (see, for example, the illustrative embodiments in DE 103 04 448 A1 or WO 03/097859 A2).

In addition to the detection of glucose, other types of detection of various analytes are known, especially from the field of medicine. For example, in O. Hofmann et al.: Towards microalbuminuria determination on a disposable diagnostic microchip with integrated fluorescence detection based on thin-film organic light-emitting diodes, Lab Chip, 2005, 5, 863-868, a method is described for detection of HSA (human serum albumin). The method is based on a reaction of HSA with the dye albumin blue 580, which generates a strong emission at 620 nm when excitation takes place with a light of suitable wavelength.

Other chemical and/or biochemical forms of optical detection are also known from the prior art. For example, U.S. Pat. No. 6,331,438 B1 discloses a series of dyes that can be used for detecting molecular oxygen. Other types of analytes can also be detected directly or indirectly in this way.

Particularly in the area of mobile chemical analysis, environmental analysis or medical diagnostics, however, a problem is that conventional optical detection methods, which require complex apparatus (e.g. large-volume light sources with monochromators, lasers or photometers), are not really practicable, particularly for portable use. Therefore, in the prior art, various attempts have been made to make available test devices or test elements based on partial integration of one of the described optical detection methods. For example, EP 0 811 154 B1 discloses an optical fluorescence sensor based on an indicator molecule which is embedded in a polymer matrix. For the fluorescence detection, a photodetector, an excitation light-emitting diode and an indicator membrane are integrated as components into the fluorescence sensor.

EP 0 244 394 B1 discloses a microstructured sensor element which is used for determining substance concentrations in gaseous and liquid samples and which has a carrier layer and an indicator layer. A substrate, in which at least one photosensitive element is integrated, is arranged on the carrier layer. This substrate has at least one area that is permeable to the excitation radiation for excitation of the indicator substance.

U.S. Pat. No. 4,889,690 discloses a sensor arrangement which is used to measure physical parameters or concentrations of particles and which comprises a laminar light source. Indicator particles that fluoresce under excitation by the laminar light source are embedded in an indicator layer, the fluorescence light being detected by a photoelectric receiver.

U.S. Pat. No. 6,331,438 B1 discloses an optical sensor used for detecting chemical, biological or physical analytes. Here, an analyte-sensitive layer is optically coupled to a thin-film electroluminescence layer. The optical response of the analyte-sensitive layer to the excitation light is picked up by a photodetector.

From the article by B. Choudhury et al., already cited above, an arrangement for glucose detection is known which is based on excitation of a dye that emits in the red spectral range and is embedded together with glucose oxidase in an indicator layer. This arrangement uses what is called a "reverse face detection method" in which the indicator layer is excited through a glass substrate by means of an organic light-emitting diode (OLED). The fluorescence light is measured by means of a photomultiplier (PMT), also after passing through the glass substrate.

A detection device for detecting HSA is known from the already cited article by O. Hofmann et al. There, a microstructured chip is used in which a liquid sample containing the analyte is conveyed into a detection chamber. Excitation takes place there by means of an organic light-emitting diode, and fluorescence light is conveyed to a spectrometer by means of a spectrometer fiber and is analyzed.

However, the devices and methods known from the prior art have numerous disadvantages in terms of practical use, in particular in terms of their use in portable medical diagnostics, and it is these disadvantages that have hitherto prevented widespread use in chemical analysis or medical diagnostics. For example, many of the disclosed methods are associated with extremely complex assembly of components, such as the sensor element disclosed in EP 0 811 154 B1. Because of their high production costs, such sensor elements cannot really be used for one-off tests in particular. Even in cases where it is only individual parts of such sensors that have to be replaced, the complex replacement procedure prevents use in portable medical diagnostics, where elderly patients and children, for example, have to operate such devices. The sensor element known from EP 0 244 394 B1, and involving complex inorganic microstructuring methods such as lithography techniques or the like, is also not really practicable for many areas of medical diagnostics, because of its complexity and because of the high production costs associated with the microstructuring methods.

The devices known from U.S. Pat. No. 4,889,690, from U.S. Pat. No. 6,331,438 B1, from the aforementioned publication by B. Choudhury et al., and also from the abovementioned publication by O. Hofmann et al, are also associated with various disadvantages, which in particular relate to the use of elaborate detection devices for the fluorescence light. For example, in the devices used by B. Choudhury et al. and O. Hofmann et al., a large-volume photomultiplier or even a spectrometer and fiber system are necessary, which largely rules out their use in portable medical diagnostics. Similarly complex is the photodetector disclosed in U.S. Pat. No. 6,331,438 B1, which is arranged separately from the actual test device and can be used for a time-resolution method, and which must therefore have a correspondingly complex design. The sensor element disclosed in U.S. Pat. No. 4,889,690, and based on the use of electro-chemoluminescent radiation sources, requires high operating voltages and at the same time provides low light output, thus greatly increasing the demands placed on the photodetector used.

A further disadvantage of the devices disclosed in U.S. Pat. No. 6,331,438 and in the publication by B. Choudhury et al. is that the layer structures shown entail a glass substrate being coated on both faces. Such devices coated on both faces are difficult to produce in practice, particularly since the application of a metal layer on one face of the substrate at the same time leads to contamination of the reverse face of the substrate, which cannot even be avoided by complex protective measures. Also, handling of sensitive substrates coated on both faces, in particular an inexpensive automated handling, is difficult to achieve in practice. Moreover, test elements coated on both faces are more difficult for a patient to use.

SUMMARY

The present invention makes available an integrated test element that permits detection of at least one analyte in a sample, in particular in a liquid sample. The test element should in particular be suitable for use in portable analysis, in particular in portable medical diagnostics, and should be inexpensive, reliable, easy to produce and also easy to handle, and the abovementioned disadvantages of the devices known from the prior art should be avoided as far as possible. The present invention is achieved by an integrated test element with one or more of the features described herein.

An "integrated" test element is to be understood here in particular as a test element that is designed in one piece, not taking into account one or more electronic control and/or evaluation devices that may optionally be required. Separate electrical leads or contacting devices that may be required, and also a fully integrated (hybrid) design (see, for example, DE 102 53 154 A1), are consistent with and covered by this definition.

The integrated test element is used for detecting at least one analyte in a sample. This can preferably involve fluid samples, that is to say gaseous or liquid samples, in particular liquid samples, for example blood or blood constituents, urine or other body fluids used in the field of medical diagnostics. However, depending on the field of application, for example in chemical analysis or in environmental technology, other types of samples may be considered, for example simple ambient air, liquid reaction mixtures or the like.

Also, the expression "the at least one analyte to be detected" is to be interpreted broadly, depending on the field of use. Referring to the abovementioned prior art, it can relate, for example, to one or more inorganic or organic molecules that are detected directly or indirectly. The following explanations relate essentially to detection of glucose, but without limiting the scope of application of the invention.

The proposed integrated test element for detecting at least one analyte in the sample has at least one carrier element. In contrast to many of the devices known from the prior art, this carrier element does not necessarily have to be a transparent carrier element, such as a sensitive glass substrate, for example. In practice, glass substrates are generally used in organic light-emitting diodes or other organic electronic components, because glass has good barrier properties against moisture and oxygen and therefore protects the sensitive organic and metal substances of the components. However, since test elements, in particular test elements in medical analysis, are in many cases stored dry and only have relatively short operating times, such stringent requirements in respect of the carrier element can often be dispensed with in test elements.

Thus, the carrier element can in principle be made of any desired rigid or flexible material. Carrier elements of complex composition, for example multi-layer structures, are also possible. For example, the carrier element can include a flexible plastic and/or glass substrate, for example a plastic film, e.g. a PET film, or also a glass substrate, for example a thin, flexible glass substrate, it being possible, for example, to make use of thin glasses that are commercially available in layer thicknesses of about 50 to 100 µm. Paper, cardboard and/or ceramic substrates, or substrates made from plastic materials, are also possible. Thus, in contrast to the test elements known from the prior art, the carrier element can be adapted to the particular purpose. For example, in order to reduce the cost and/or weight of the test elements, it is possible to use carrier elements with paper and/or plastic substrates, which permits use as a disposable article, for example.

The carrier element has an application face. This application face (it can also be an application face made up of several surfaces) can have various shapes depending on the configuration of the carrier element, for example a flat shape and/or a curved shape, for example the shape of a cylinder surface or of a cone. It is preferable if the application face, at least in some areas, has the least possible surface roughness. This is of advantage for the construction of organic electronic components (see below), since voltage peaks are avoided in this way, and the useful life and reliability of the components are increased. In other areas, however, a rough surface can alternatively or additionally be used, for example in order to achieve increased light scattering by the carrier element, so as to adapt the optical characteristics of the carrier element specifically to the intended purpose (e.g. increased excitation by diffuse excitation light).

If appropriate, the surface roughness of the application face can be improved by subsequent working (e.g. polishing) and/or by application of additional smoothing layers (which then are a constituent part of the at least one carrier element), for example organic smoothing layers. Such techniques are known from the field of production of organic light-emitting diodes in which, for example, Cu-phthalocyanine, polyaniline (PANI) or inorganic smoothing layers, for example silicon dioxide or the like, can be used. By means of such smoothing layers, which can be applied to the carrier element by, for example, a wet chemical process or a gas phase process (e.g. physical vapor deposition (PVD) or chemical vapor deposition (CVD)), the surface roughness of the application face of the carrier element can be adjusted in the desired area.

At least one organic electroluminescent component, in particular at least one thin-film component, preferably at least one organic light-emitting diode (OLED), is applied to the application face of the carrier element. The at least one organic electroluminescent component can be applied to the application face of the carrier element directly or, alternatively or in addition to this, it can be applied to the application face of the carrier element with interpositioning of further intermediate layers. Additional components can also be inserted between the application face of the carrier element and the at least one organic electroluminescent component.

The structure and the composition of the at least one organic electroluminescent component are known to a person skilled in the art. Without limiting the invention, it is also assumed that the at least one organic electroluminescent component is at least one organic light-emitting diode (OLED). The structure of such OLEDs is described, for example, in U.S. Pat. No. 6,331,438 B1, in the aforementioned publication by B. Choudhury et al., and also in the above-described publication by O. Hofmann et al. Further possibilities regarding the structure of OLEDs are known to a person skilled in the art. It is possible to use what are called "small molecule" components, that is to say components composed essentially of monomers or oligomers as organic materials, or alternatively or additionally also components composed of organic polymer materials. Illustrative embodiments of the latter components are described, for example, in K.-T. Wong et al: Ter(9,9-diarylfluorene)s: Highly Efficient Blue Emitter with Promising Electrochemical and Thermal Stability, J. Am. Chem. Soc. 124, 11576, 2002. Hybrid components, that is to say components using small molecules and also polymer materials, can also be used. The proposed structure is not limited to a specific layer structure or a specific material combination.

The structure of the OLED can be adapted to the special requirements of the integrated test element, for example to the environment in which it is used or to the indicator substance employed (see below). In this way, for example, it is possible to use OLEDs with different spectral characteristics, in particular emission characteristics adapted to the indicator substance employed. Thus, an optimal excitation wavelength can be chosen. Instead of an individual OLED, it is also possible to use several OLEDs arranged next to one another or over one another, for example a matrix of OLEDs. In this way, for example, a color mixture or addition of several OLEDs can also be achieved. Such components are also known from the prior art, in particular from display technology. It is also possible to use OLEDs whose spectral emission characteristics can be specifically influenced by external parameters, for example the operating voltage and/or the operating current, such that these components can be varied spectrally, for example.

Apart from their differences in terms of the choice of materials and in terms of their precise configuration and layer structure, a common feature of the OLEDs is in each case a basic sandwich structure. This sandwich structure involves one or more organic layers (small molecules and/or polymers) which are embedded between two electrodes, an anode and a cathode. Charge carriers, electrons and holes pass from these electrodes into the organic materials, where they are transported, in order subsequently to impinge on one another and, with emission of photons, to emit light. OLEDs are normally composed of several organic layers that perform different functions. Thus, charge injection layers can directly adjoin the electrodes, charge transport layers can be used, and recombination layers can be included in which a particularly efficient recombination can take place with generation of photons of the desired wavelength. Such layer structures are known to a person skilled in the art. The choice of suitable electrode materials is also known, it being customary to use an anode material with high work function, for example transparent indium tin oxide (ITO). In this way, the energy barrier between the Fermi level of the anode material and the corresponding level of the adjoining organic layer (e.g. the so-called highest occupied molecular orbital, HOMO, of the organic layer) is kept as low as possible (e.g. in the range of less than 100 meV) for efficient injection of positive charge carriers. Correspondingly, in order to minimize the energy barrier upon injection of negative charge carriers, a metal cathode material with low work function is customarily used, for example calcium or magnesium, followed by a cover layer. Other materials are also possible, for example the use of a thin lithium-fluoride layer in combination with an aluminum electrode as cathode. Overall, the organic layers usually have layer thicknesses in the range of between 50 nm and 300 nm, whereas the electrode layers usually each have a thickness of several hundred nanometers.

The integrated test element also has at least one photodetector element. This at least one photodetector element is also preferably arranged on the application face of the test element, although another arrangement is also possible, for example an arrangement on the reverse face. As will be described in detail below, the at least one photodetector element can be arranged between the carrier element and the at least one OLED, over the at least one OLED and/or in the same plane as the at least one OLED. A matrix of several photodetector elements is also possible.

It has proven particularly advantageous if the at least one photodetector element has at least one organic thin-film photodetector element. Such organic thin-film photodetector elements are described in U.S. Pat. No. 5,523,555, in U.S. Patent App. Pub. No. 2003/0066950 A1 or in U.S. Pat. No. 5,698, 048, for example. Organic monomers, oligomers or polymers can be used as organic materials, and, similarly to OLEDs, layer structures composed of several layers can be used. Organic thin-film photodetector elements of this kind are accordingly constructed similarly to the construction of organic light-emitting diodes, for example as a sandwich structure between an indium-tin oxide electrode and an aluminum electrode. The irradiation of light into the organic layers or organic layer of the at least one organic thin-film photodetector element causes a separation of charge carriers in the organic layer or layers, such that a voltage forms between the electrode layers and can be detected. It is also possible for a current to be detected. For the measurement, the photodetector element can be operated with or without an electrical bias voltage. Moreover, an integrated pre-amplifier circuit can already be contained completely or partially in the integrated test element, for example in conventional silicon technology, or preferably also in organic technology, for example the organic operation amplifier circuit shown in DE 102 53 154 A1.

The integrated test element also has at least one indicator substance on the application face. This at least one indicator substance is designed to alter at least one optical characteristic, in particular an emission characteristic, preferably a fluorescence characteristic (hereinafter also referred to as photoluminescence) when the at least one indicator substance comes into contact with the at least one analyte to be detected. The at least one indicator substance is arranged on the application face of the integrated test element in such a way that excitation light, emitted by the at least one organic electroluminescent component, can pass at least partially into the at least one indicator substance.

The nature and configuration of the at least one indicator substance depends on the analyte that is to be detected. Thus, it is possible in principle to use all of the indicator substances known from the prior art, for example dyes which alter their fluorescence behavior on account of the presence or absence of oxygen. Since an important area of application of the present invention lies in the detection of glucose in body fluids, the above-described detections using glucose oxidase and corresponding oxygen-detecting dyes according to the publication by B. Choudhury et al. are preferred, or also the detections using glucose dehydrogenase and NAD, as are described, for example, in DE 103 04 448 A1 or WO 03/097859 A2. The term indicator substance is to be interpreted broadly, such that it can also be composed, for example, of different indicator substances for different analytes. The indicator substance can also have a structure made up of several layers, or the indicator substance can comprise an indicator matrix with one or more indicators introduced into this indicator matrix, similarly to the structure described in U.S. Pat. No. 4,889,690.

The function of the indicator substance corresponds substantially to the functions of the devices known from the prior art. Thus, the at least one indicator substance reacts to the presence or absence of the at least one analyte to be detected and accordingly alters its reaction to the irradiation of the excitation light irradiated from the at least one organic electroluminescent thin-film component. For example, in the presence of the at least one analyte, a photoluminescence of the at least one indicator substance can be increased or reduced. This change is detected by means of the at least one photodetector element, and, using a control and evaluation electronics unit that can be designed as a separate circuit or as a circuit completely or partially integrated into the test element (see below), it is possible, on the basis of a known correlation (e.g. an empirically determined and stored correlation) between an analyte concentration and the photoluminescence intensity, to draw a conclusion regarding the analyte concentration at a predetermined intensity of the excitation light.

Accordingly, a test system for detecting at least one analyte is proposed, which comprises at least one integrated test element according to the above description and also at least one control and evaluation electronics unit with means for controlling the at least one organic electroluminescent component, means for reading out the at least one photodetector element, and means for calculating at least one analyte concentration from the known correlation between the alteration of the at least one optical characteristic of the at least one indicator substance and the concentration of the at least one analyte.

The proposed integrated test element and the proposed test system have numerous advantages over the test elements and test systems known from the prior art. Thus, the advantages of using an organic electroluminescent component are essentially combined with integration of the at least one photodetector element. The use of organic electroluminescent components, in particular of one or more OLEDs, greatly reduces the production costs, since it is possible to do without expensive external light sources, for example inorganic light-emitting diodes. The production costs of organic light-emitting diodes are a fraction of what it would cost to produce corresponding inorganic components or other types of light sources. Accordingly, the proposed integrated test elements can also be used as disposable test elements, which affords a considerable advantage in terms of hygiene, reliability and reproducibility. Moreover, the integration of the at least one OLED into the proposed integrated test element has the effect that, in contrast to external light sources, the positioning of the light source relative to the at least one indicator substance does not change, which also greatly increases the reliability and robustness of the measurement.

The integration of the at least one photodetector element into the integrated test element also has the effect that, for example, fluorescence light from the at least one indicator substance always passes into the at least one photodetector element under the same spatial conditions. This too greatly increases the degree of precision, since, in the usual measurement structures, even the very slightest changes in the geometry of the measurement structure can greatly influence the results. Optical apertures (and thus the light incidence) are essentially determined (light spots, stops) by the planar properties of the structures (resulting from the simple production methods, e.g. vapor deposition, sputtering, printing, exposure, etc.). With the proposed structure, by contrast, the light signal to be measured can be coupled directly into the at least one photodetector element, which can effect an improved signal quality and signal strength at a constant excitation energy.

It also proves advantageous that all the functional components of the integrated test element, that is to say the at least one organic electroluminescent thin-film component, the at least one indicator substance and the at least one photodetector element, are all advantageously arranged on the application face of the test element. In this way, in contrast to the device described for example in the publication by B. Choudhury et al., it is possible to produce test elements which are plane, but which are sensitive to mechanical influences or contamination only on one face. Test elements of this kind, for example test strips, can thus readily be placed with their uncoated face onto a support, without thereby damaging the test elements. This represents a considerable advantage in terms of the handling of such test elements. It is also possible, in this way, to avoid using expensive and sensitive transparent substrates.

The use of organic thin-film photodetector elements also leads to very advantageous structures of the test elements. Thus, it is possible in particular to produce test elements which have a hybrid organic/silicon structure or even an all organic structure, that is to say an integrated structure with integrated excitation source, integrated indicator substance and integrated detector which, apart from possible metal electrodes, are composed entirely of organic materials. It is thus possible to avoid complex hybrid technology, which is necessary for the combination of inorganic components (e.g. inorganic light-emitting diodes) with organic components. Despite the use of possibly different materials, similar production methods can be employed for all the components of the test elements.

The proposed integrated test element and the proposed test system according to the above description can be advantageously refined in various ways. In one refinement, the at least one indicator substance is at least partially in direct physical contact with the at least one organic electroluminescent component, in particular bordering the latter, and/or is at least partially identical to it. For this purpose, a layer of the at least one indicator substance can be, for example, applied to an OLED directly or with interpositioning of an optically transparent intermediate layer. However, it is also possible for an indicator substance and a planar OLED to be arranged in the "same plane" next to each other, such that light from the OLED, which is emitted parallel to the layer plane, can pass directly into the indicator substance, without having to pass through one of the electrodes of the OLED. In this way, less stringent demands are placed on the transparency of the electrodes of the OLED. In this way too, the optical paths are greatly shortened, such that the effects of reflections, scattering or other light losses are reduced. It is also possible in this way to greatly reduce the dependency of the detection on the geometry of the components of the integrated test elements.

Direct contact between the indicator substance and the at least one organic electroluminescent component can also be achieved, for example, if the at least one indicator substance is completely or partially integrated, in particular merged and/or chemically bound, into at least one organic layer of the at least one organic electroluminescent component. Thus, the at least one indicator substance can be part of an OLED, for example if enzymes, coenzymes and/or dyes, forming a constituent part of the indicator substance, are incorporated into a polymer matrix of the OLED and/or are introduced as an independent layer into the OLED. In this way, the excitation of the at least one indicator substance and the corresponding reaction of the at least one indicator substance, for example by photoluminescence, take place in one and the same organic layer structure. The output (e.g. the number of excited indicator molecules per photon emitted by the OLED) is in this way considerably increased, since, for example, a molecule of the indicator substance can be surrounded by light-emitting molecules of the OLED and is thus excited isotropically. Light losses can be considerably reduced in this way, and photodetector elements can be used with much less stringent demands on their efficiency.

In another advantageous embodiment of the integrated test element, the at least one carrier element has at least one needle-shaped and/or cannula-shaped and/or lancet-shaped part for piercing of and/or insertion into a body tissue. Thus, for example, the integrated test element can be designed completely or partially in the form of a needle, for example in order to be inserted into interstitial fatty tissue. The proposed integrated test element can thus also be advantageously used for long-term measurements, for example. It is also possible for a cannula-shaped test element to be inserted, followed by aspiration of blood or other body fluid or body tissue, for example by means of a vacuum pump, by means of capillary forces or by means of suitable suction materials, after which an analyte concentration, for example a glucose concentration, is measured inside the cannula ("puncture test" or "measuring cannula").

For application of the at least one organic electroluminescent component, the at least one photodetector element and the at least one indicator substance, it is possible, for example, to use techniques which are known from the field of optical fiber technology and in which organic layer structures, in combination with electrode layers, are applied to optical fibers. Such techniques are known to a person skilled in the art and can be found, for example, in M. Sampietro: Organic Photodetectors: A Possible Technology for On-Fiber Receivers, SPIE, volume 4943, 116-123, 2002.

In another advantageous embodiment of the integrated test element, the excitation light emitted by the at least one organic electroluminescent component can be completely or partially prevented from reaching the at least one photodetector element. This ensures that the at least one photodetector element does not simultaneously measure excitation light and fluorescence light, for example, which would make evaluation of the signal much more difficult. Such an embodiment can, for example, have at least one optical filter element and/or at least one light-blocker element, for example in combination with a suitable geometry of the structure. For example, a 90° geometry can be used in which, as has been described above, the OLED and the indicator layer lie in one layer plane, whereas the at least one photodetector element is arranged in another layer plane. Moreover, at least one optical filter element can also be arranged in front of the at least one photodetector element. In another embodiment, an OLED and a photodetector element are arranged "next to each other" in one layer plane, separated by a "light blocker element", for example a photoresist web, which is at least partially non-transparent for the excitation light. For example, a photoresist can be used which itself has suitable properties ensuring that light cannot pass through it. Alternatively or in addition, it is also possible, for example, for dyes to be incorporated into the photoresist. Other materials are also conceivable for the "light blocker element", for example plastics (e.g. polyimides) or inorganic materials. Integration of the light blocker element into the carrier element is also conceivable, for example by formation as an injection-molded part or the like. On top of this layer plane, a layer of the indicator substance is then applied, for example, such that excitation light can pass from the OLED into the indicator substance, while fluorescence light emitted by the indicator substance can then pass again into the photodetector element. Such structures, which are simple to produce, greatly facilitate the evaluation of the generated signals, since no correction has to be made in respect of the excitation light.

In another advantageous embodiment of the integrated test element and of the test system, at least one reference device is provided. This proposed at least one reference device is designed to alter at least one optical characteristic, in particular a reflection characteristic and/or an emission characteristic, in particular a fluorescence characteristic, depending on the intensity of the excitation light emitted by the at least one organic electroluminescent component, said alteration of the at least one optical characteristic being at least substantially independent of the presence or absence of the at least one analyte. This at least one optical characteristic of the at least one reference device should be able to be measured by means of the at least one photodetector element.

In other words, the at least one reference device can be used to obtain up-to-date information on the emission characteristics of the OLED and/or the detection characteristics of the at least one photodetector element, which information is independent of the presence or absence of the at least one analyte to be detected. In this way, it is possible, for example, to detect ageing processes of the OLED and/or of the photodetector element and to correct these accordingly. This aspect is of considerable importance since organic electronic components in particular are still to some extent associated with considerable problems regarding their useful life and their quality, which could adversely affect the reliability or long-term stability of the test elements. By means of the at least one reference device, it is thus possible to acquire calibration data, for example at any time during a measurement, in order to compensate for such degradation effects of the components, in particular of the organic components. A static reference measurement is preferably used. However, time-resolved reference measurements are also conceivable, for example reference measurements in which a decay behavior of a fluorescence reference over time is recorded. However, such time-resolved measurements in some cases require complex evaluation circuits, such that a static reference measurement is preferred overall. Use of the at least one reference device for quality control is also conceivable, for example in order to detect if an OLED (e.g. as a result of a component failure or as a result of age-related degradation) no longer generates enough excitation light for carrying out a detection. In this case, a warning signal can be generated, for example, or a corresponding error routine can be performed.

For example, the at least one reference device can contain a simple reflection layer and/or a simple reference fluorophore, for example titanium dioxide and/or a brightener known from the paper industry and/or the luminescence pigment "LUMILUX®" from Honeywell. With a predefined control of the OLED (e.g. with a constant control current), the signal of the at least one photodetector element, which detects light emitted or reflected by the reference fluorophore, is measured continuously. A drop in this photodetector element signal can, for example, point to a degradation of the OLED or a degradation of the photodetector element. A simple quotient formation with the originally measured photodetector signal can thus lead to a correction factor, with which the signals originating from the at least one indicator substance are also multiplied. In this way, reliable measurement values can be generated even in the event of degradation of the integrated test elements. It is in this way also possible to eliminate effects which, for example, have an influence on the action of the at least one detectable analyte, or of the body fluid in which the at least one detectable analyte is contained, on the component properties of the OLED or of the photodetector element, for example if an OLED and/or a photodetector element contained in the at least one reference device are exposed to the same conditions as corresponding components in the other areas of the test element. This refinement of the invention thus contributes greatly to the usability of organic electronic components in medical diagnostics.

In another advantageous refinement, the at least one organic electroluminescent component and/or the at least one photodetector element is composed of several individual components. In particular, the at least one organic electroluminescent component and/or the at least one photodetector element can be configured as a matrix, similar to the structures known from display technology. In this way, the failure of individual components can be compensated for, or certain areas of the integrated test element can be provided with different indicator substances, for example for detection of a number of different analytes.

The test system according to the invention, and according to the above description, can also be advantageously refined as such. In accordance with the concept of providing the at least one integrated test element with at least one reference device, the test system can also be refined such that said test system has at least one correction electronics unit, wherein the at least one correction electronics unit is designed to correct the calculation of the at least one analyte concentration on the basis of the information generated by means of the at least one reference device according to the above description. It will be noted in this connection that, in this embodiment and in other embodiments, the at least one control and evaluation electronics unit can be arranged completely or partially on the at least one integrated test element itself or also in a separate read-out device. In the case of integration on the integrated test element, an integrated circuit is recommended, for example, in the form of a conventional integrated circuit (IC), or also a complete or partial configuration as an organic electronic circuit. For the latter purpose, it is possible to use, for example, organic thin-film transistor circuits known to persons skilled in the art. This refinement is in line with the above-described concept of an "all-organic" system and additionally reduces the cost of producing the test elements.

A method for producing an integrated test element in accordance with the above description is also proposed according to the invention. This method is explained in greater detail in connection with the following illustrative embodiments. The illustrative embodiments are shown in the figures. Identical reference numbers designate elements that are identical in structure or that correspond to one another in terms of their function.

BRIEF DESCRIPTION OF THE FIGURES

FIG. 5 shows an illustrative embodiment of a method for producing an integrated test element according to FIG. 1A.

FIG. 6 shows a method for producing an integrated test element according to the illustrative embodiment in FIG. 1C.

DETAILED DESCRIPTION OF THE ILLUSTRATED EMBODIMENTS

Figure 1A:
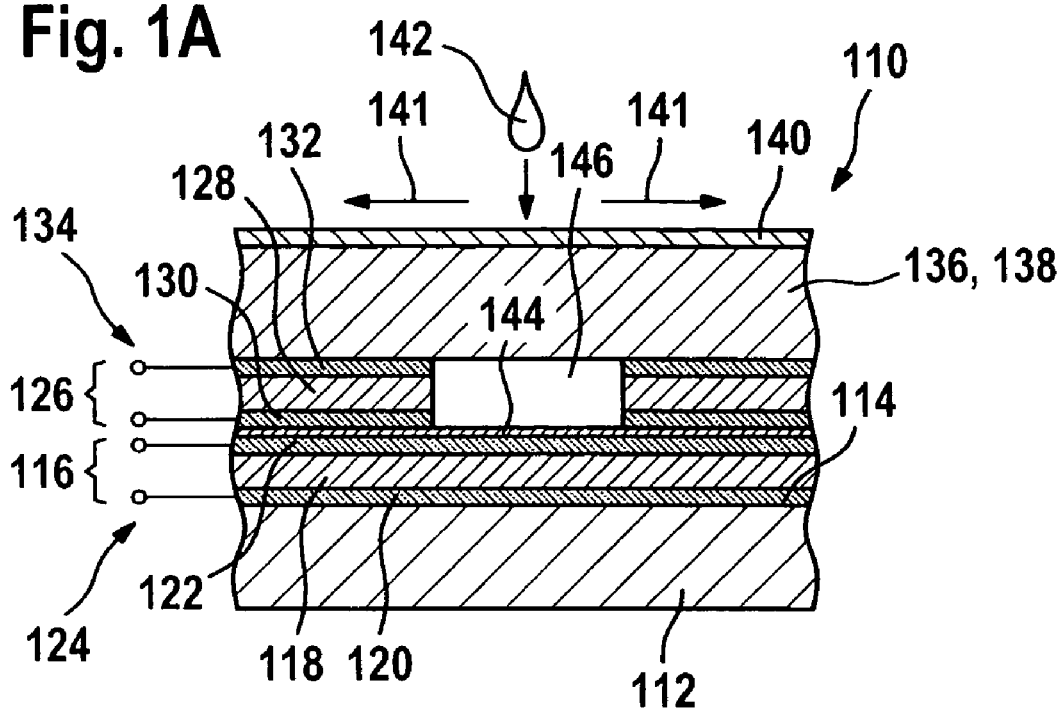
FIGS. 1A to 1E show various schematic layer structures of illustrative embodiments of an integrated test element according to the invention.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Various illustrative embodiments of layer structures of integrated test elements 110 according to the invention are depicted in FIGS. 1A to 1E. The integrated test elements 110 all have a carrier element 112 which, according to the above description, can be made of glass, plastic, ceramic or paper substrate, for example, and has an application face 114. In these illustrative embodiments according to FIG. 1A to FIG. 1E, the integrated test elements 110 also have organic thin-film photodetector elements 116. These organic thin-film photodetector elements (hereinafter abbreviated to "OPD") are designed, for example, as a sandwich structure in accordance with the prior art cited above. One or more organic layers 118 are embedded between a first electrode 120 and a second electrode 122. Regarding the choice of the organic materials, reference is made to U.S. Pat. No. 5,698,048 or to U.S. Patent App. Pub. No. 2003/0066950 A1, for example. The electrodes 120, 122 are contacted (e.g. by suitable structuring or separate leads) by means of electrode contacts 124 shown symbolically in FIG. 1A. The contacting is effected analogously in the illustrative embodiments according to FIGS. 1B to 1E.

Moreover, the integrated test elements 110 according to the illustrative embodiments in FIGS. 1A to 1E have organic light-emitting diodes (OLEDs) 126. Like the OPDs 116, the OLEDs 126 are also designed as a sandwich structure, wherein one or more organic layers 128 according to the above description are embedded between a first electrode 130 and a second electrode 132. The first electrode 130 and the second electrode 132 are in turn electrically contacted by electrode contacts 134, which are shown symbolically only in FIG. 1A.

Moreover, the integrated test elements 110 according to the illustrative embodiments in FIGS. 1A to 1E have indicator substances 136. In the illustrative embodiments according to FIGS. 1A, 1B, 1D and 1E, the indicator substance 136 is designed as a separate indicator layer 138, whereas in the illustrative embodiment according to FIG. 1C the indicator substance 136 forms a constituent part of the organic layers 128 of the OLED 126. The indicator substance 136 is designed according to the above description and is adapted to the analyte that is to be detected.

For example, the indicator substance can be designed according to the examples given in DE 103 04 448 A1 or WO 03/097859 A2.

Moreover, the integrated test element 110 has a barrier layer 140 which covers the integrated test element 110 and which is permeable to what is in this case a liquid sample 142 containing the analyte to be detected, or at least permeable in respect of the analyte, but which at the same time prevents escape of constituents of the indicator substance 136. This barrier layer 140, which is optional and can also be dispensed with depending on the intended purpose, ensures, in the case of an implanted integrated test element 110, that enzymes or coenzymes acting as cytotoxins cannot pass from an indicator layer 138 into the blood stream or into the body fluid. In applications outside of the body, this barrier layer 140 can also be dispensed with. Moreover, the barrier layer 140 can also optionally have an influence on the sample 142 that is to be analyzed. For example, the barrier layer can separate this sample 142 into different constituents. Effects of this kind are known, for example, as "sprite action", in which a blood sample is separated such that red blood cells are divided off. Such layers with a "sprite action", by means of which plasma can be separated from whole blood, are known, for example, from EP 0 457 183 A1 or from U.S. Patent App. Pub. No. 2004/0222168 A1, of which, for example, the layer in EP 0 457 183 A1 has glass fibers coated with polyvinyl alcohol/polyvinyl acetate. Other layers with the same or similar effects can also be used. This "sprite function" is indicated symbolically in FIG. 1A by the arrows 141. In extracorporeal applications, it is not absolutely essential to use biocompatible materials. In this case, there is greater freedom regarding the choice of materials of the barrier layer 140, such that, for example, it is possible to use a polyurethane and also other plastics, for example polyimides, or even inorganic cover materials.

The illustrative embodiments of the integrated test elements 110 according to FIGS. 1A to 1E differ in terms of the arrangement and sequence of the OPDs 116, the OLEDs 128 and the indicator substance 136. Thus, in the illustrative embodiment according to FIG. 1A, the OPD 116 is arranged in a first layer plane, as viewed from the direction of the carrier element 112. The OPD 116, which in this illustrative embodiment is designed as a large-surface OPD (another format is also possible), is followed by an optical filter element 144, which can be constructed for example as an organic layer (e.g. one or more polymer layers) or as an inorganic layer, and which prevents excitation light from reaching from the OLED 126 to the OPD 116. In a second layer plane, the OLEDs 126 are then constructed on this optical filter element 144. In the view according to FIG. 1A, these OLEDs are composed of several individual OLEDs 126 between which a space 146 remains. In practice, this space 146 will also fill completely or partially with indicator substance 136, but this does not impair the function of the component.

In a third layer plane, the indicator layer 138 is finally applied on the OLEDs 126 and is closed off from the outside by the barrier layer 140. The material that can be used for the barrier layer is, for example, a polyurethane, or the above-mentioned materials with sprite action.

In this "three-layer" structure according to FIG. 1A, excitation light passes into the indicator layer 138 from the OLEDs 126, in which preferably the second electrode 132 is designed as transparent electrode (for example as ITO electrode or thin, transparent metal electrode). There, a photoluminescence is generated depending on whether the analyte to be detected, in particular glucose, is present or absent. This photoluminescence is generally of a longer wavelength than the excitation light. Thus, it has proven advantageous in practice to use OLEDs 126 with blue emission light, as can be done, for example, in the above-mentioned article by K.-T. Wong et al., by means of suitable fluorene compounds. In the structure according to FIG. 1A, the photoluminescence light of longer wavelength then passes through the space 146 (and partially also through the OLEDs 128 too) and through the optical filter element 144 into the OPD 116, of which the second electrode 122 is for this purpose advantageously made completely or partially transparent, analogously to the second electrode 132 of the OLED 126. The optical filter element 144 is chosen such that the photoluminescence light of the indicator layer 138 is not blocked or is blocked only insignificantly.

Figure 1B:
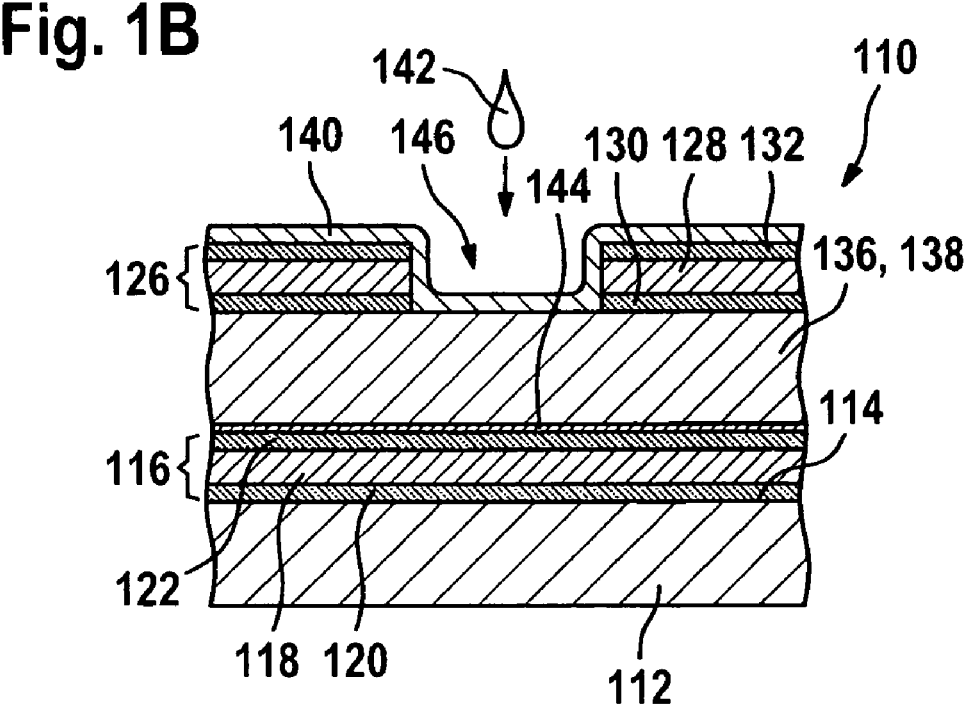

FIG. 1B shows an illustrative embodiment which, analogously to FIG. 1A, is also made up of three layers. In contrast to FIG. 1A, however, the arrangement of the OLEDs 126 and of the indicator layer 138 is changed in sequence. Thus, in this example, the OPD 116 is adjoined by the indicator layer 138, which in turn is adjoined by the OLEDs 126. In this case, the barrier layer 140 adjoins the OLEDs 126, the sample 142 being able to reach the indicator layer 138 through the space 146 between the OLEDs 126. In this illustrative embodiment according to FIG. 1B, the first electrodes 130 of the OLEDs 126 are preferably transparent, such that excitation light can reach from the OLEDs 126 into the indicator layer 138. Analogously to FIG. 1A, the second electrode 122 in the OPD 116 is transparent, such that photoluminescence light can reach from the indicator layer 138 into the organic layers 118 of the OPD 116.

Figure 1C:
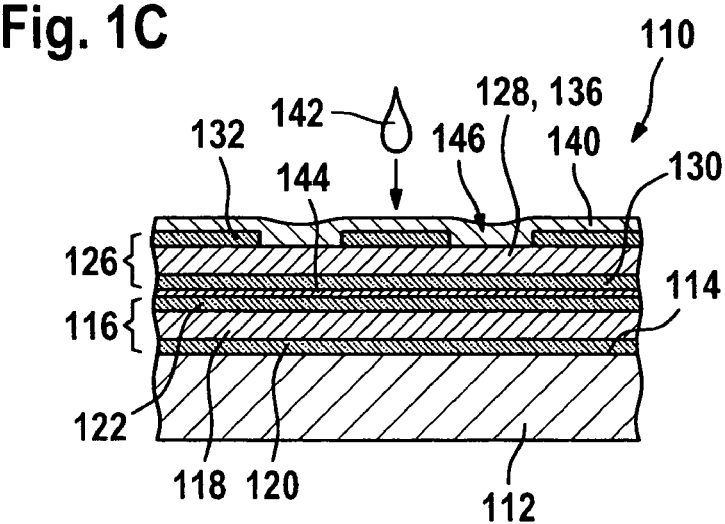
Figure 1D:
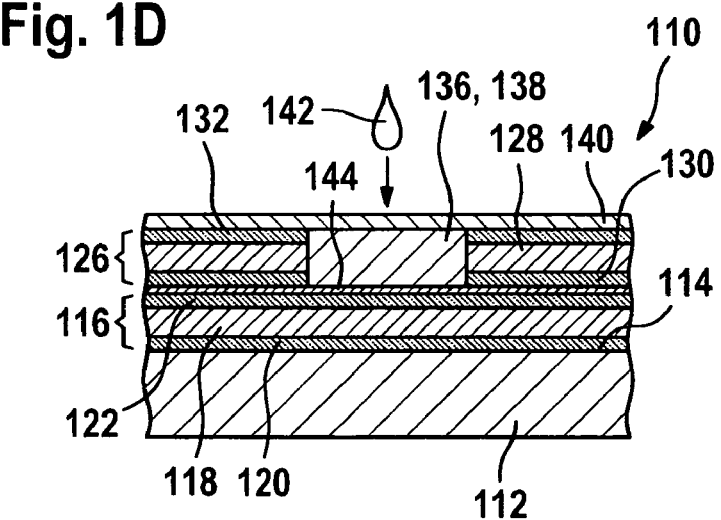

In the illustrative embodiments according to FIGS. 1C and 1D, two-layer structures are shown in each case. However, they are differently configured. Thus, in the illustrative embodiment according to FIG. 1C, as described above, the indicator substance 136 is merged into one or more organic layers 128 of the OLED 126. In this way, excitation light source and indicator function coincide within the OLED 126. This entails, as has been described above, the advantage of greater light efficiency. Moreover, in the illustrative embodiment according to FIG. 1C, the OPD 116 has a large-surface format, although other formats are also possible. This OPD 116, arranged in a first layer plane, is adjoined by the optical filter element 144, followed by the OLED 126 in a second layer plane. The second electrode 132 of the OLED 126 is structured in this illustrative embodiment, such that, between the portions of this second electrode 132, spaces 146 remain free through which the sample 142 can penetrate into the organic layers 128 of the OLED.

In this illustrative embodiment, as also in the illustrative embodiment according to FIGS. 1B and 1D, the barrier layer 140 at the same time protects the second electrodes 132 of the OLEDs 126. The structuring of the second electrodes 132 of the OLEDs 126 can be adapted to the needs of the integrated test element 110, for example with a rectangular or circular space 146, for example in order to be able to apply a droplet of blood as liquid sample 142.

FIG. 1D shows a layer structure which, analogously to FIG. 1C, is made up of two layers. Here, however, the indicator substance 136 is not merged into the organic layers 128 of the OLED 126, but instead lies in a separate indicator layer 138, which is arranged in the same layer plane as the OLEDs 126. For this purpose, the integrated test element 110 according to FIG. 1D again has an OPD 116, which is arranged in a first layer plane and adjoined by an optical filter element 144. Arranged on the optical filter element 144, there are discrete OLEDs 126 which, however, do not completely fill the second layer plane, and between which an indicator layer 138 is introduced. This two-layer structure is again closed off by a barrier layer 140.

In this illustrative embodiment according to FIG. 1D, the OLEDs 126 are used as so-called "edge emitters". In edge emitters of this kind, the excitation light generated by the organic layers 128 does not pass through one of the two electrodes 130, 132, but instead exits parallel to the layer plane, that is to say parallel to the electrode layers 130, 132, and is conveyed into the indicator layer 138. For this reason, none of the electrodes 130, 132 needs to be made transparent in this illustrative embodiment according to FIG. 1D. This affords considerable advantages, since the production of a transparent electrode, in particular of an ITO electrode, may in practice be associated with considerable difficulties, particularly if this transparent electrode, which is usually generated by an aggressive production process (various plasma processes), is intended to be applied to an underlying organic layer structure. In the illustrative embodiment according to FIG. 1D, this problem is avoided, since in this case both electrodes 130, 132 can be designed as metal electrodes, for example, which are much easier to produce than transparent electrodes.

Analogously to the above description, the excitation light of the OLED 126 excites the indicator substance 136 in the indicator layer 138 to photoluminescence, depending on whether the analyte is present or absent. This photoluminescence light then passes through the transparent second electrode 122 of the OPD 116 into the organic layers 118 of the OPD 116 and generates a corresponding signal. In this illustrative embodiment, therefore, excitation light and photoluminescence light are in a "90° arrangement". Depending on the geometry, that is to say in particular depending on the distance of the individual OLEDs 126 from one another, this 90° structure itself ensures that excitation light cannot pass from the OLEDs 126 into the OPD 116. To this extent, the requirements placed on the optical filter element 144 in this illustrative embodiment are much less stringent, such that in some circumstances this optical filter element 144 can also be completely dispensed with.

Figure 1E:
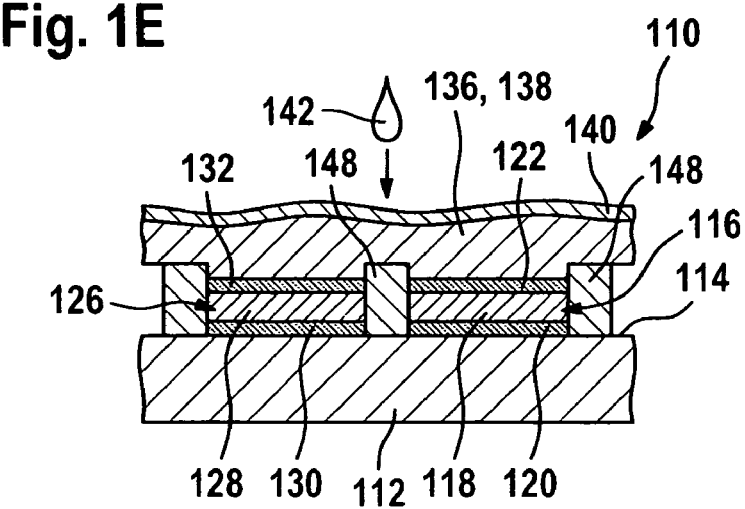

In FIG. 1E, finally, another two-layer illustrative embodiment is shown in which the OLED 126 and the OPD 116 are arranged in a first layer plane, followed by an indicator layer 138 in a second layer plane lying above this. In this illustrative embodiment, the second electrodes 122, 128 of the OPD 116 and of the OLED 126 are each transparent. Between OLED 126 and OPD 116, light-blocker elements 148 are arranged which prevent excitation light from reaching from the OLED 126 into the OPD 116. These light-blocker elements 148, in this illustrative embodiment, are designed as separating webs which, for example, can be generated by means of a lithographic photoresist process. Thus, the separating webs can, for example, be composed of photoresist, and the photoresist can also be colored in order to increase non-transparency to light at the excitation wavelength. In addition, however, an optical filter element 144 (not shown in FIG. 1E) can also be applied to the second electrode 122 of the OPD 116, which filter element 144 additionally suppresses crossover of excitation light via the indicator layer 138 into the OPD 116.

In this illustrative embodiment according to FIG. 1E, excitation light passes from the OLED 126 through the transparent second electrode 132 into the indicator layer 138 and excites photoluminescence therein, depending on whether the analyte to be detected is present or absent, and the photoluminescence light passes through the transparent second electrode 122 into the organic layers 118 of the OPD 116, so as to be detected in this way. Once again, the indicator layer 138 is closed off from the outside by the barrier layer 140. The structure according to FIG. 1E is comparatively simple and inexpensive to produce, since OPD 116 and OLED 126 require basically the same construction methods and only have different organic layers 118, 128. An additional barrier layer (not shown) can also be introduced between the first layer plane with the OLEDs 126 and OPDs 116 and the second layer plane with the indicator substance 136, for example in order to protect the OLEDs 126 and OPDs 116 from the chemical actions of the indicator layer 138. Construction of the OLEDs 126 and OPDs 116 is followed by application of the indicator layer 138, which can be done by a coating process with considerably fewer quality demands than in the case of the OLEDs 126 and OPDs 116, for example by a simple dipping method (see below). To this extent, the structure according to FIG. 1E offers numerous advantages.

The production of an integrated test element 110 will be described using the example of the test elements 110 according to FIGS. 1A and 1C and by reference to FIGS. 5 and 6. The production method according to FIG. 5 describes the production of an integrated test element 110 according to the example in FIG. 1A, whereas the method according to FIG. 6 leads to an integrated test element 110 according to the example in FIG. 1C. The method steps are shown schematically in FIGS. 5 and 6 in a preferred sequence. It will be noted that, in addition to the method steps shown, other method steps not shown here can also be carried out, and that the method steps do not necessarily have to be performed in the sequence shown. It is also possible for individual method steps to be repeated.

In the production of an integrated test element 110 according to the structure in FIG. 1A by the method shown in FIG. 5, the carrier element 112 forms the initial base. In method step 510, the first electrode 120 of the OPD 116 is applied to the carrier element 112 to the carrier element 112. As has been described above, this first electrode 120 does not necessarily have to be a transparent electrode, such that this electrode can be designed, for example, as a metal electrode, for example an aluminum electrode. The first electrode 120 can therefore be applied, for example, by means of a conventional vapor-deposition or sputtering technique. Other application techniques are also possible, for example chemical vapor deposition (CVD), or even the use of conductive polymer materials as electrodes, which, for example can be pressed on or spun on.

This first method step 510 of the method according to FIG. 5 is not necessarily part of the production method since, in some circumstances, substrates as carrier elements 112 can also be acquired commercially which already contain this first electrode 120 of the OPD 116, for example substrates which are already coated with an electrode layer (e.g. ITO) by the manufacturer.

In method step 512, the first electrode 120 of the OPD 116 is structured. The type of structuring depends on the nature of the first electrode 120. If, for example, ITO or metal electrodes are used as first electrode 120, then an etching technique is recommended, for example, in which the first electrode 120, in a suitable etching bath, is removed from the application face 114 at the desired locations with the aid of a lithography procedure. Alternatively, a laser ablation method can also be used, for example. Laser ablation methods can also be used, for example, in order to generate necessary conductor tracks, for example for chip integration into the integrated test element 110 and/or for complex electrode geometries, for example in the context of needle-shaped integrated test elements 110. Electrodes or conductor tracks other than the first electrode 120 can also be structured in this way.

As an alternative to method step 512, it is also possible, in method step 510 involving application of the first electrode 120, to use methods by means of which the first electrode 120 is applied in an already structured form onto the carrier element 112. In each case, either by structuring during application or by subsequent structuring according to method step 512, it is possible in this way to produce first electrodes 120 of the OPD 116 which, for example, contain leads or large-surface portions on which the OPD 116 is built.

In method step 514, the at least one organic layer 118 of the OPD 116 is applied. Regarding the type and nature of these organic layers, reference is made to the abovementioned prior art, for example U.S. Pat. No. 5,698,048. Depending on the nature of the organic materials, this step can involve, for example, the use of wet chemical methods (e.g. spin coating, printing of a solution or similar wet chemical methods), or gas phase processes can also be used, for example chemical vapor deposition (CVD) or physical vapor deposition (PVD), for example vapor deposition in vacuum. Wet chemical methods are of course recommended for polymers and oligomers, whereas gas phase processes are more suitable for monomers as organic materials (small molecules). Overall, it is advantageous to adapt many of the method steps described here to large-scale continuous serial production processes, for example a so-called "reel-to-reel process", such that overall, for example, printing techniques and/or laminating techniques or similar large-scale processes are preferably to be chosen for the method described here.

This application of the organic layers 118 in method step 514 can also be structured. Thus, for example, vapor deposition of organic layers can be carried out through a suitable shadow mask. In this way, areas of the integrated test element 110 in which no organic layers 118 are wanted remain uncovered. Alternatively or in addition, and this will be recommended particularly in wet chemical methods, areas can also be subsequently exposed, for example by means of a lithographic process or a material removal process, for example a laser ablation process.

Thereafter, in method step 516, the second electrode 122 of the OPD 116 is applied. Regarding the method, reference is made here to method step 510. However, a difficulty in the structure according to FIG. 1A is that the second electrode 122 should be at least partially transparent to photoluminescence light emitted by the indicator layer 138. Accordingly, it is possible here to use, for example, a thin metal layer which still has sufficient transparency (e.g. a metal layer of several 10 nm). Alternatively, an ITO electrode can also be used, wherein ITO is deposited onto the organic layers 118 usually by means of a sputtering process.

Here too, a structuring of the second electrode 122 can be carried out during application, or subsequent structuring can be carried out. Because of the sensitivity of the organic layers 118 to subsequent structuring processes, it is preferable for the second electrode 122 of the OPD 116 to be applied in an already structured form, that is to say, for example, by application through a suitably configured shadow mask.

In method step 518, the optical filter element 144 is applied to the second electrode 122 of the OPD 116. Again, a person skilled in the art will choose a process adapted to the type and nature of the optical filter element 144. As has been described above, the optical filter element can, for example, be one or more layers of a polymer, such that a wet chemical process is once again recommended here. Monomers or oligomers can also be used, or organic substances that cross-link or polymerize in situ, that is to say after application. Accordingly, gas phase processes can also once again be used. It is also possible to use inorganic materials. A further possibility is to apply the optical filter element 144 as a film or so-called "stand-alone layer", for example by means of a film layer of an optical filter element 144 being fitted or adhesively bonded as a whole onto the OPD 116.

Thereafter, in method step 520, the first electrodes 130 of the OLED 126 are applied to the optical filter element 144. Since said electrodes in this illustrative embodiment do not necessarily have to be transparent electrodes (indeed, transparent electrodes are even a disadvantage here, since excitation light would then pass directly into the OPD 116), they can be metal electrodes, for example. Reference is thus made to method step 510. Here too, however, it is recommended for the electrodes 130 to be applied in an already structured form (e.g. by means of a shadow mask technique or a suitable printing technique), in order to avoid subsequent structuring steps, which could damage the layers already applied underneath. Alternatively or in addition, however, it is also possible to subsequently structure the first electrodes 130 of the OLED 126.

In method step 522, the at least one organic layer 128 of the OLED 126 is applied to the first electrodes 130. Once again, the coating process is preferably adapted to the type and nature of the organic materials used, such that reference can be made in this context to method step 514. However, in method step 522, a structuring of the organic layers 128 of the OLED 126 is generally required, since, in the illustrative embodiment according to FIG. 1A, it is necessary to create the space 146 through which photoluminescence light can pass from the indicator layer 138 to the OPD 116. Alternatively, however, it is also possible for the photoluminescence light to pass through the OLEDs 126. In the latter case, it would be preferable for the first electrode 130 of the OLED 126 also to be made transparent. For the structuring of the organic layers 128 of the OLED 126, a shadow mask technique is again recommended in the case of application from the gas phase, for example. In the case of wet chemical application, it is possible, for example, to use printing techniques (e.g. ink-jet printing, screen printing or web-offset). Subsequent structuring, for example by means of laser ablation or lithographic techniques, is also conceivable once again, but this is less preferable, because of the sensitivity of the layers already applied underneath.

Thereafter, in method step 524, the second electrodes 132 of the OLED 126 are applied. As has been described above in the illustrative embodiment according to FIG. 1A, these are advantageously transparent electrodes, such that reference can be made to method step 516 concerning application. In this case, however, a structuring is once again generally required in order to create the space 146. A shadow mask technique is therefore once again recommended. However, other techniques are also conceivable. Thereafter, in method step 526, the indicator layer 138 is applied. Here too, the coating technique depends on the choice of materials. Thus, for example, an indicator substance 136, for example a mixture of enzymes, coenzymes and dyes, can be introduced into an organic matrix, for example a polymer matrix or a gel (see, for example, DE 103 04 448 A1 or WO 03/097859 A2). The material of this matrix should be at least partially permeable to the sample 142, at least in respect of the analyte, in order to ensure that the analyte can reach the indicator substance 136. Wet chemical methods are then recommended for the application, for example printing, spin-on methods, or simple dip and/or drip methods. Although structuring is not generally necessary, it can nevertheless also be carried out, for example in order to expose electrode contacts 116, 126 of the OPD 116 or OLED 126 for contacting.

Thereafter, in method step 528, the barrier layer 140 is optionally applied, for example also by a dip method or by application from the gas phase. Application as a separate structural part, for example in the form of an affixable film, is also conceivable, as is also the case for the indicator layer 138.

After method step 528, the integrated test element 110 is in principle ready for use. Testing, calibrating or the like can then be carried out to determine, for example for a defined batch of integrated test elements 110, the correlation between analyte concentration and OPD signal, or to test the individual components. Thus, for example, random samples from a batch of test elements 110 can be measured, after which a correction function is determined with which this batch is coded and which is stored in the correction electronics unit (e.g. a control processor 323 and/or a first evaluation electronics unit 320, see below concerning FIG. 3) and, if appropriate, can be output via a display.

The construction of the integrated test element 110 according to the illustrative embodiment in FIG. 1C will be explained on the basis of the schematic chart in FIG. 6 and in a manner analogous to FIG. 5. The structure as far as the first electrode 130 of the OLED corresponds substantially to the illustrative embodiment according to FIG. 1A, although in this illustrative embodiment according to FIG. 1C the first electrode 130 of the OLED 126 is not structured. Alternatively or in addition, structuring can also be carried out here. In line with the similar or identical structure, the method steps 610 to 620 correspond to the method steps 510 to 520 according to the method in FIG. 5. However, it should be noted here that the first electrode 130 of the OLED 126 in the illustrative embodiment according to FIG. 1C is preferably transparent, such that there are slight differences in respect of method step 620 compared to method step 520, said differences involving a different choice of material (e.g. ITO or a thin metal electrode) in the example according to FIG. 1C. These differences, however, will be readily evident to a person skilled in the art.

In parallel with or after method steps 610 to 620, preparations are made to apply the indicator layer 138. For this purpose, in method step 622, the indicator substance (for example a mixture of enzymes, coenzymes and dyes, see above) is incorporated into one or more organic materials of the organic layers 128 of the OLED 126. If, for example, polymer OLEDs are used, this incorporation can be done by stirring the indicator substance 136 in during the preparation of polymer solutions, which are customarily used for a wet chemical application of the polymer layers of the OLED 126. Care should be taken to ensure that the indicator substance is compatible with the solvents that are to be used for the solutions. The layer can be chosen accordingly. For example, indicator substances that are incompatible with organic solvents can be incorporated into aqueous solutions that are normally used for some of the organic layers 128 of the OLED 126.

Accordingly, in method step 624, the organic layers 128 of the OLED 126 are then built up, for example by a wet chemical process, for example by spinning on or printing on. The mixture containing the indicator substance and the OLED substance, and prepared in method step 622, is then used for one or more of the at least one organic layer 128 of the OLED 126. Instead of a solution, it is of course also possible by analogy to use a dispersion or suspension. Thus, in method step 624, the organic layers 128 of the OLED 126 are applied.

As an alternative to the illustrative embodiment of the method as shown in FIG. 6, methods are also possible, and covered by the invention, in which method steps 622 and 624 are at least partially combined. Thus, the incorporation of the indicator substance 136 into one or more of the organic layers 128 of the OLED 126 can also be carried out, alternatively or in addition, during the application of the organic layers 128 of the OLED 126. In a wet chemical process, this can be done, for example, by a solution of an indicator substance and a solution of an OLED substance being spun on or printed on simultaneously. In the case of application from the gas phase, a co-evaporation or co-sputtering process is recommended, for example, or application from several chemical sources in a CVD process.

In method step 626, the second electrode 132 of the OLED 126 is then applied, analogously to method step 524 in FIG. 5. Here too, a structured application is once again preferred, for example by vapor deposition using a shadow mask. It is possible in this way- to create the spaces 146 through which the sample 142 can penetrate into, or reach, the organic layers 128 of the OLED 126.

Thereafter, in method step 628, the barrier layer 140 is applied in a manner analogous to method step 528 in the illustrative embodiment according to FIG. 5.

Figure 2A:
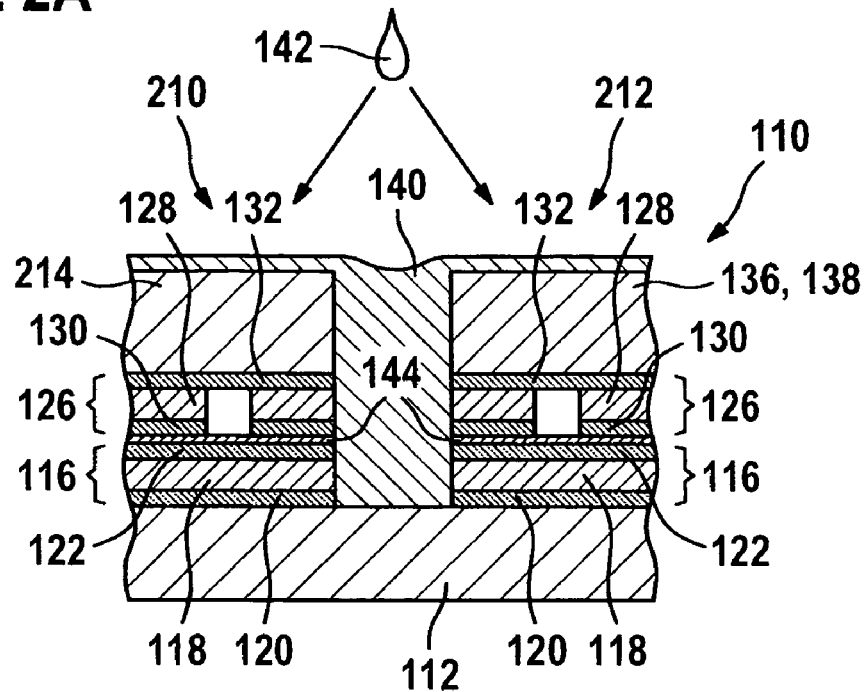
FIGS. 2A and 2B show illustrative embodiments of an integrated test element with a reference device.
Figure 2B:
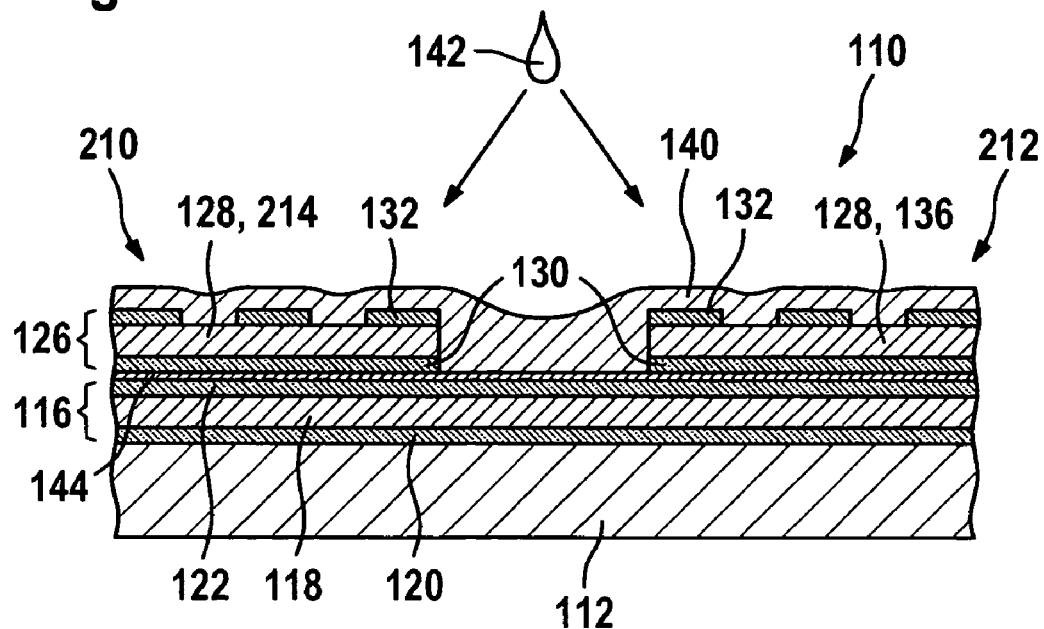

FIGS. 2A and 2B show two different illustrative embodiments of an integrated test element 110 according to the invention, each of them having a reference device 210. In the illustrative embodiment according to FIG. 2A, the actual measurement device 212 is formed in the right-hand part and arranged in a layer structure similar to the layer structure according to the illustrative embodiment in FIG. 1A. Formed on a carrier element 112, there is the layer structure of an OPD 116, followed by an optical filter element 144. The latter is adjoined by the layer structure of the OLEDs 126, analogously to FIG. 1A. The indicator layer 138, which contains the indicator substance 136, is built up on the OLEDs 126. Regarding the function of this measurement device 212, reference is made to the description of the illustrative embodiment in FIG. 1A.

At the same time, however, in the illustrative embodiment according to FIG. 2A, the reference device 210 is also arranged on the carrier element 112 of the integrated test element 110. This reference device, in the example according to FIG. 2A, again first of all comprises an OPD 116, analogously to the measurement device 212. This OPD 116 is covered by an optical filter element 144, followed by OLEDs 126, analogously to the measurement device 212.

However, in the example according to FIG. 2A, the OLEDs 126 are not adjoined by an indicator layer 138, but by a layer of a reference fluorophore 214. This can be, for example, a diffuse scattering layer and/or a pure reflection layer with which excitation light irradiated by the OLEDs 126 is reflected into the OPD 116 of the reference device 210. The OLEDs 126 and the OPDs 116 of the reference device 210 are preferably identical or at least similar to the OLEDs 126 and OPDs 116 in the measurement device 212. To this extent, the reference fluorophore 214 can also be a wavelength-shifting substance, for example a dye, which, regardless of the presence or absence of an analyte, emits a wavelength-shifted fluorescence, which in turn can be picked up by the OPD 116. For reference device 210 and measurement device 212 to be designed as similarly as possible, the spectral characteristics of this reference fluorophore 214 are preferably chosen similar to the indicator substance 136 in the indicator layer 138 of the measurement device 212.

The OPDs 116 of the measurement device 212 thus deliver a signal which, as has been described above, allows a conclusion to be drawn regarding the presence or absence and also the concentration of the analyte to be detected (or analytes to be detected) in the sample 142. However, as has been described above, this signal is associated with some uncertainty, for example on account of variations in the characteristics of the components or on account of ageing, and can be variable in time. Accordingly, as has been described above, the signal of the reference device 210 is used, which signal is subject to similar variations. By quotient formation or similar correction algorithms, for example, errors and signal drifts can thus be compensated. An influence of the sample 142 on the characteristics of the components can also be compensated in this way since, for example, a liquid sample 142 can influence the nature, useful life and/or brightness of the OLEDs 126 and OPDs 116. Overall, it is possible in this way to compensate for multiple influences, and measures can also be taken, if appropriate, in order to separately measure and correct additive influences, for example dark currents.

It will also be noted that a reference device 210 does not in principle have to contain a reference fluorophore 214, since, for example, the OPDs 116 of the reference device 210 can directly pick up the excitation light of the OLEDs 126 as reference. This suffices in principle for quotient formation. Moreover, an optical filter element 144 is not directly needed in the reference device 210. However, it has been found in practice that it is expedient for the layer structure of the reference device 210 to be made as similar as possible to the measurement device 212, in order to generate values that are as comparable as possible and, consequently, to permit a correction that is as reliable as possible.

FIG. 2B shows an illustrative embodiment, analogous to FIG. 2A, of an integrated test element 110 with a reference device 210. Once again, the integrated test element 110 has a reference device 210 and a measurement device 212 on the same carrier element 112. The structure and function of the measurement device 212 correspond to the structure of the integrated test element according to the illustrative embodiment in FIG. 1C. This means that an OPD 116 (a format with several OPDs 116 is also possible) is adjoined by an optical filter element 144, followed by an OLED 126 in which an indicator substance 136 is incorporated in at least one organic layer 128. A structure with a separate layer of the indicator substance 136 in the OLED 126 is also conceivable. Regarding the function and structure of the measurement device 212, reference is made to the above description of FIG. 1C.

In this illustrative embodiment according to FIG. 2B, the reference device 210 and the measurement device 212 share the photodetector 116 and the optical filter element 144. Alternatively, however, other embodiments are also possible with separate OPDs 116 and separate filter elements 144.

The reference device 210 again has an OLED 126, which in principle can correspond to the structure of the OLED 126 in the measurement device 212. However, in this illustrative embodiment, a reference fluorophore 214 is incorporated into the organic layers 128 of the OLED 126 of the reference device 210 or applied as a separate layer. Regarding its structure, the comments on the indicator substance 136 apply analogously. Thus, in the same way as in the description of FIG. 2A, the reference device 210 again supplies a signal that is independent of the presence or absence of the at least one analyte in the sample 142. Here too, in principle, it is alternatively possible to dispense completely with a reference fluorophore 214 in the OLED 126, in line with what has been said above regarding FIG. 2A.

Although the measurement device 212 and the reference device 210 share the same OPD 116, in this illustrative embodiment according to FIG. 2B, this can still lead to separate measurement and reference signals, for example by means of a pulsed measurement pattern (multiplexing in frequency and time). As has been described above, an embodiment with separate OPDs is also possible.

Figure 3:
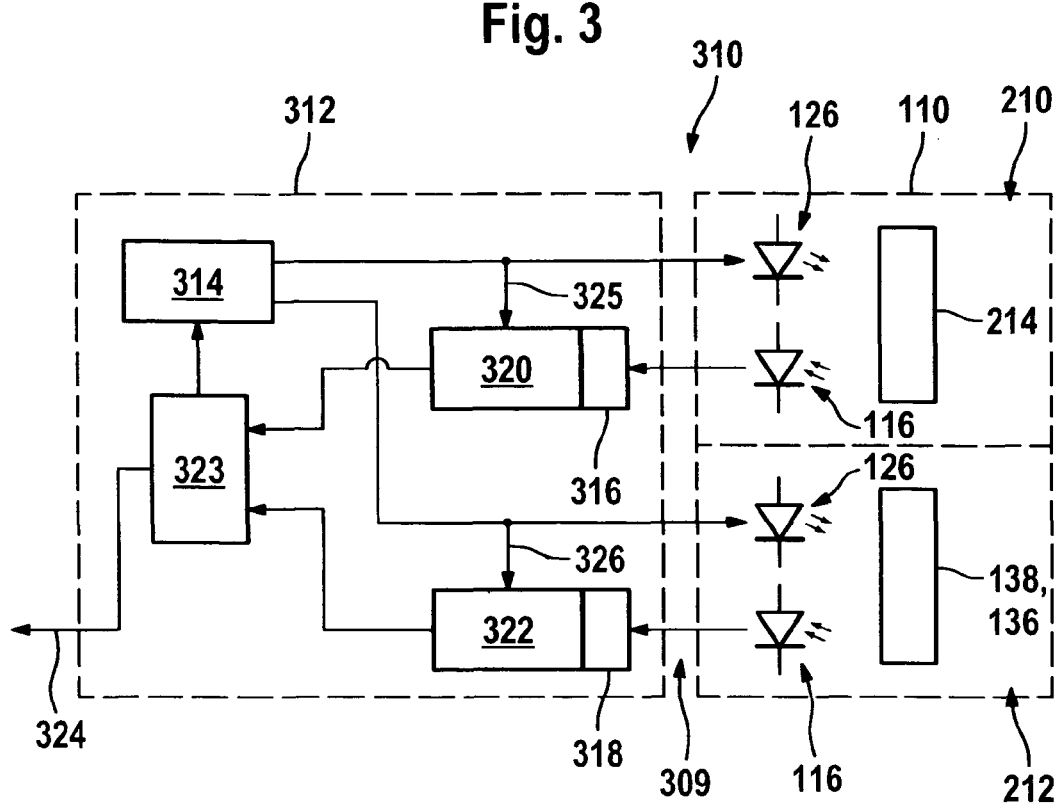
FIG. 3 shows an illustrative embodiment of a test system comprising an integrated test element with a reference device.

FIG. 3 shows a test system 310 for detecting at least one analyte in a sample 142, which system uses an integrated test element 110 with a reference device 210. It is assumed hereinbelow that the integrated test element 110 is structured according to the illustrative embodiment in FIG. 2A. In principle, however, it is possible to use any desired integrated test elements 110 with reference device 210.

The test system 310 has an integrated test element 110, which is indicated symbolically in FIG. 3. The integrated test element 110 comprises a reference device 210 and a measurement device 212, each of which have OLEDs 126 and OPDs 116. As in FIG. 2A, the reference device 210 comprises a reference fluorophore 214, and the measurement device 212 comprises an indicator layer 138 with an indicator substance 136. Other structures are also possible.

The test system 310 also comprises a control and evaluation electronics unit 312, which can be constructed separately from the integrated test element 110 (for example as part of a measuring appliance) or which can also be embodied completely or partially as part of the integrated test element 110, for example in the form of a printed circuit or an IC. The control and evaluation electronics unit 312 and the integrated test element 110 are connected, for example, via an interface 309, for example an interface having one or more plug connectors. In the case of complete or partial integration of the control and evaluation electronics unit 312, this interface can also be entirely or partially dispensed with or can be replaced by corresponding leads.

The control and evaluation electronics unit 312 comprises a control circuit 314 for operating the OLEDs 126 in the measurement device 212 and the reference device 210. The embodiment of this control circuit 314 of the OLEDs 126 is known to a person skilled in the art. For example, it can involve one or more simple current sources which supply the OLEDs 126 with current of constant strength in a pulsed or continuous manner. Customary operating voltages are in the range of between 1 and 10 volts. More complex drive circuits are also possible, such that, for example (see above), a pulsed control of the OLEDs 126 can also be effected, for example in combination with time-resolved evaluation. Control with constant voltage is also conceivable, but this is less advantageous since the luminosity of the OLEDs 126 is generally proportional to the control current. The OLEDs 126 of the measurement device 212 and of the reference device 210 can also be controlled separately or also jointly by the control circuit 314. It is also possible, for example, to take account of thermal effects, which take into account and/or suitably correct a change in the intensity of the OLEDs 126 by heating.

Moreover, in this illustrative embodiment according to FIG. 3, the control and evaluation electronics unit 312 comprises a first OPD amplifier 316 for controlling and evaluating the OPD 116 of the reference device 210, and a second OPD amplifier 318 for controlling and evaluating the OPD 116 of the measurement device 212. The OPD amplifiers 316, 318 basically serve to pick up the signals generated by the OPDs 116 and, if appropriate, to correspondingly evaluate them, that is to say to carry out, for example, a preliminary processing, filtering, etc. OPDs 116 can also be partially operated with a bias voltage, which in this case can likewise be supplied by the OPD amplifiers 316, 318.

Moreover, in the illustrative embodiment according to FIG. 3, the control and evaluation electronics unit 312 has a first evaluation electronics unit 320 which is fed with signals from the control circuit 314 of the OLEDs 126 and with signals from the first OPD amplifier 316 and, if appropriate, is also synchronized from the control circuit 314 (indicated symbolically in FIG. 3 by the arrow 325). As has been described above, the first evaluation electronics unit 320 calculates a correction factor, for example, which takes into account an ageing of the OLEDs 126 and/or OPDs 116. Thus, for example, the first evaluation electronics unit 320 (and also the entire control and evaluation electronics unit 312) can be completely or partially embodied as a microprocessor, and, for example at a constant current strength with which the OLEDs 126 are operated, a quotient is formed from the signal delivered by the first OPD amplifier 316 and from the current strength signal from the control circuit 314 of the OLEDs 126. Initially, for example, this quotient can be randomly assigned the correction factor 1. If the quotient drops during the operation of the test system 310 or of the integrated test element 110, then proportionally smaller correction factors are accordingly generated.

Moreover, the control and evaluation electronics unit 312 has a second evaluation electronics unit 322, which operates analogously to the first evaluation electronics unit 320 and which is fed with signals from the control circuit 314 of the OLEDs 126 and with signals from the second OPD amplifier 318 and, if appropriate, is synchronized by the control circuit 314 (indicated symbolically in FIG. 3 by arrow 326). The signals of this second evaluation electronics unit 322, like the signals of the first evaluation electronics unit 320, are forwarded to a control processor 323. The control processor 323 can, for example, comprise means which determine an analyte concentration in the sample 142 from the signals of the second OPD amplifier 318 and from the control signals of the control circuit 314 of the OLEDs 126. For example, this correlation can be stored as a calculating rule (e.g. "concentration is proportional to the OPD signal at predetermined OLED current"), and/or look-up tables can also be defined, for example, which permit a correlation and evaluation. It is also possible for batch-specific data relating to a batch of integrated test elements 110 to be contained in this calculating rule or in this evaluation information. Other configurations of the evaluation electronics unit 322 are also conceivable, as will be evident to a person skilled in the art. To take into account the correction which is generated by the first evaluation electronics unit 320 and which, for example, points to a degradation of the OLEDs 126 or OPDs 116, the determined analyte concentration can, for example, be divided by the abovementioned correction factor or multiplied by it. Other forms of correction are also conceivable, for example in which the signal generated by the first evaluation electronics unit 320 directly influences the calculation or determination of the analyte concentration. Moreover, the control processor 323 can also comprise means for generating the average and for correcting the average. In this illustrative embodiment according to FIG. 3, the control processor 323 and the evaluation electronics units 320, 322 thus form constituent parts of the above-described correction electronics unit.

The test system 310, finally, generates a measurement signal 324, which can be an analog or digital data signal, for example. This measurement signal can be converted into a corresponding measurement value in the control and evaluation electronics unit 312 itself, or it can be forwarded to additional electronic components. In this way, measurement results, in particular analyte concentrations, can be presented on a display, for example, or can be input into a database or a memory of a computer system. For example, the whole test system 310 can be designed as a compact portable measuring appliance, the integrated test element 110 being inserted into a housing with corresponding connections. Such measuring appliances are known from the prior art, such that an adaptation to the particular features of the test system 310 according to the diagram in FIG. 3 is possible for a person skilled in the art.

Figure 4:
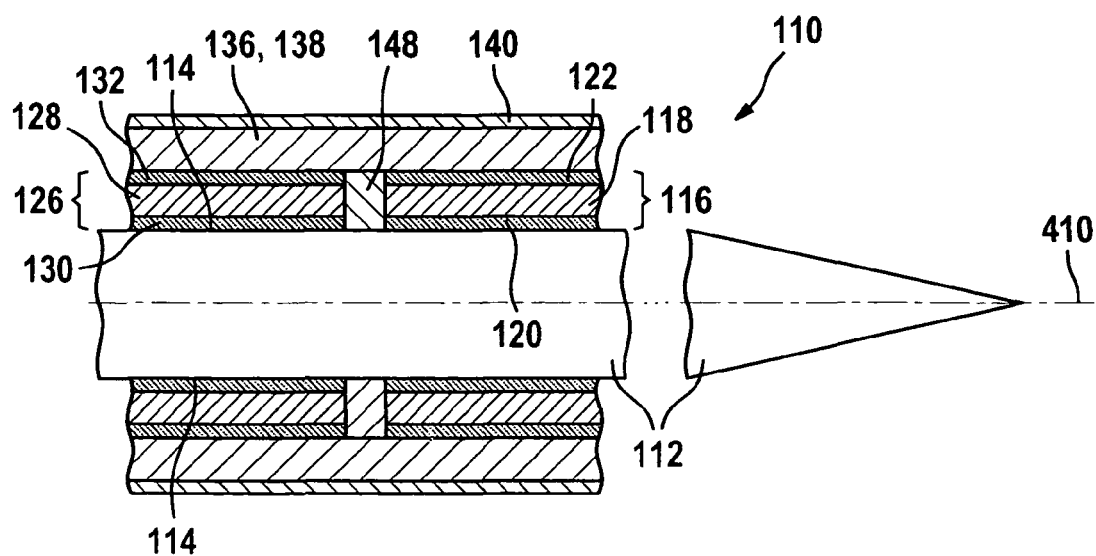
FIG. 4 shows a schematic cross section through an integrated test element corresponding to the structure in FIG. 1E, with a needle-shaped carrier element.

In FIG. 4, finally, an illustrative embodiment of an integrated test element 110 is shown which has a needle shape. In this illustrative embodiment, which is shown in cross section in FIG. 4, essentially the same layer structure is used as in the illustrative embodiment according to FIG. 1E. In principle, however, all other layer structures are possible, for example the layer structures according to FIGS. 1A to 1F.

In contrast to the plane configuration according to FIG. 1E, the integrated test element 110 in the illustrative embodiment according to FIG. 4 is rotationally symmetrical about the axis of symmetry 410. In this illustrative embodiment, the carrier element 112 is designed as a rotationally symmetrical, needle-shaped element. The OLEDs 126 and the OPD 116, which are separated from each other by the light-blocker element 148, are applied on this carrier element 112 in a first layer "plane" (that is to say in fact as hollow cylinder layers). Alternatively, embodiments are possible with several OLEDs 126 and/or several OPDs 116. The OPD 116 and the OLEDs 126 are adjoined, in a second layer "plane", by the indicator layer 138, followed by a barrier layer 140. Regarding the function of the integrated test element according to FIG. 4, reference is made to the description of FIG. 1E.

The needle-shaped integrated test element 110 according to the example in FIG. 4 is suitable, for example, for implantation in body tissue, for example in interstitial fatty tissue. For this purpose, the integrated test element 110 can, for example, be pushed directly into the body tissue. Alternatively, the integrated test element 110 can also be inserted into a cannula, which in turn is inserted into the body tissue. In this way, the integrated test element 110 can remain in the body tissue, for example for a duration of about one week, and can continuously provide measurement values.

For the production of the needle-shaped integrated test element 110 according to the illustrative embodiment in FIG. 4, reference is made, for example, to the abovementioned publication by M. Sampietro et al. The layer technologies disclosed therein for applying organic detectors to optical fibers can be transposed directly to the construction of the integrated test element 110 according to FIG. 4. Application of superposed OLEDs 126 and OPDs 116, followed by one or more indicator layers 138, is also conceivable, similar to the structure in FIG. 1C, for example. In this way, simple dip methods can be used, for example, in order to produce the individual layers of the OLEDs 126, OPDs 116 and indicator layers 138 (optionally integrated in the organic layers 128 of the OLEDs 126). In the case of implanted integrated test elements 110, an important role is played by the barrier layer 140, which can likewise be applied by a dip method for example, since, as has been mentioned above, the indicator substances used may in some cases be toxic to living human tissue.

In addition (not shown in FIG. 4), the indicator layer 138 in the illustrative embodiment in FIG. 4 can also have so-called "blood cavities". These are (for example ring-shaped or hole-shaped) indents which are provided in the indicator layer 138 (and if appropriate in the above barrier layer 140) and in which blood can accumulate, as a result of capillary effects or adhesion, and may also remain there when the needle-shaped test element 110 is withdrawn again from the body tissue. This also permits analysis outside of the body tissue.

Figure 7:
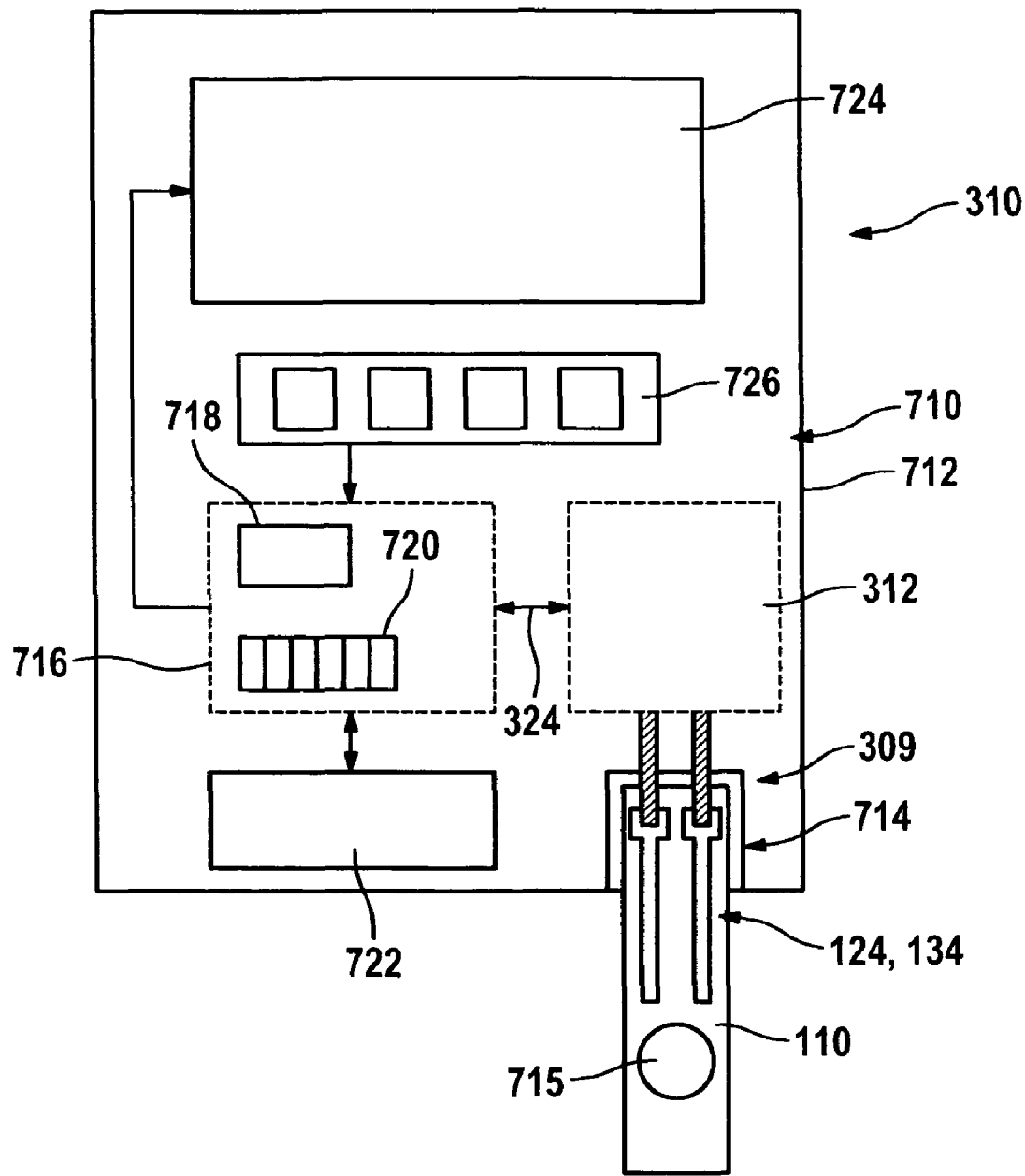
FIG. 7 shows an illustrative embodiment of a test system with a measuring appliance and an integrated test system.

Finally, FIG. 7 shows an illustrative embodiment of a test system 310 which comprises a measuring appliance 710, designed as a portable hand-held appliance, and an integrated test element 110. The test system 310 contains a control and evaluation electronics unit 312, which is connected to the integrated test element 110 via an interface 309. For example, an integrated test element 110 and a control and evaluation electronics unit 312 according to FIG. 3 can be used, such that, in this connection, reference may be made to the above description of FIG. 3. Other embodiments of the control and evaluation electronics unit 312 and/or of the integrated test element 110 are also possible.

The measuring appliance 710 has a housing 712, for example a plastic housing, with dimensions and shapes suitable for portable use. An analysis slot 714 is formed in the housing, and the integrated test element 110, designed in this illustrative embodiment as a test strip with an application zone 715 for a liquid sample 142, can be inserted into said analysis slot 714. The analysis slot 714 contains the interface 309 in which, for example by means of suitable spring contacts (not shown), the electrode contacts 124, 134 (indicated only symbolically in FIG. 7) of the OPDs 116 and OLEDs 126, respectively, are electrically contacted, analogously to the diagram in FIG. 3.

In addition to the control and evaluation electronics unit 312, the measuring appliance in FIG. 7 has a microcomputer 716. This microcomputer 716, for example, evaluates the data generated by the control and evaluation electronics unit 312 and accordingly regulates this control and evaluation electronics unit 312. In contrast to the diagram in FIG. 7, the control and evaluation electronics unit 312 can also be completely or partially a constituent part of the microcomputer 716. The microcomputer 716 can have a central processing unit 718 and one or more volatile or non-volatile data memories 720.

Moreover, the measuring appliance 710 in FIG. 7 has an energy store 722 (for example a battery), a display element 724 (for example a liquid-crystal display or an OLED display), and input elements 726 (for example one or more keys). Thus, for example, the input elements 726 can be used to operate the measuring appliance 710 and, for example, to start a measurement. Other functions of the test system 310 can also be called up in this way and utilized, for example a database function for measurement values, data processing and a graphic presentation of measurement data on the display element 724, or also a communication with other appliances, for example for the purpose of data exchange with a medical computer system (not shown in FIG. 7).

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary. Furthermore, all patents, patent applications, and publications cited herein are hereby incorporated by reference.

LIST OF REFERENCE NUMBERS 110 integrated test element
112 carrier element
114 application face
116 organic thin-film photodetector element (OPD)
118 organic layers OPD
120 1st electrode OPD
122 2nd electrode OPD
124 electrode contacts OPD
126 organic light-emitting diode (OLED)
128 organic layers OLED
130 1st electrode OLED
132 2nd electrode OLED
134 electrode contacts OLED
136 indicator substance
138 indicator layer
140 barrier layer
141 sprite function
142 sample
144 optical filter element
146 space
148 light-blocker element
210 reference device
212 measurement device
214 reference fluorophore
309 interface
310 test system
312 control and evaluation electronics unit
314 control circuit OLEDs
316 first OPD amplifier
318 second OPD amplifier
320 first evaluation electronics unit
322 second evaluation electronics unit
323 control processor
324 measurement signal/display
325 synchronization
326 synchronization
410 axis of symmetry
510 application of 1st electrode OPD
512 structuring of 1st electrode OPD
514 application of organic layers OPD
application of 2nd electrode OPD
518 application of optical filter element
520 (structured) application of 2nd electrodes OLED
522 application of organic layers OLED
524 (structured) application of 2nd electrodes OLED
526 application of indicator layer
528 application of barrier layer
610 application of 1st electrode OPD
612 structuring of 1st electrode OPD 614 application of organic layers OPD
616 application of 2nd electrode OPD
618 application of optical filter element
620 application of 1st electrode OLED
622 incorporation of indicator substance into polymer solution for OLED
624 application of organic layers OLED
626 (structured) application of 2nd electrodes OLED
628 application of barrier layer
710 measuring appliance
712 housing
714 analysis slot
715 application zone
716 microcomputer
718 central processing unit
720 data memory
722 energy store
724 display element

What is claimed is:

1. An integrated test element for detecting at least one analyte in a sample, in particular in a liquid sample, comprising: a carrier element, wherein at least one organic electroluminescent component, in particular at least one organic electroluminescent thin-film component, in particular at least one organic light-emitting diode (OLED), is applied on an application face of the carrier element, wherein the integrated test element furthermore comprises at least one photodetector element, wherein the integrated test element comprises at least one indicator substance that is at least partially integrated into at least one organic layer of the at least one organic electroluminescent component, wherein the at least one organic layer is a layer of a sandwich structure of the organic electroluminescent component and is part of one or more organic layers which are embedded between electrodes of the organic electroluminescent component such that the indicator substance is positioned between the electrodes of the organic electroluminescent component, wherein the at least one organic electroluminescent component is designed in such a way that at least some of the excitation light emitted by it reaches the at least one indicator substance, wherein the at least one indicator substance is designed to alter at least one optical characteristic, in particular an emission characteristic, in particular a fluorescence characteristic, when the at least one indicator substance comes into contact with the at least one analyte, wherein the integrated test element furthermore comprises at least one reference device which is designed to alter at least one optical characteristic, in particular at least one of a reflection characteristic and an emission characteristic, in particular a fluorescence characteristic, depending on the intensity of the excitation light emitted by the at least one organic electroluminescent component, and wherein the alteration of the at least one optical characteristic is at least substantially independent of the presence or absence of the at least one analyte.

2. The integrated test element as claimed in claim 1, wherein the at least one photodetector element includes at least one organic thin-film photodetector element.

3. The integrated test element as claimed in claim 1, wherein the at least one photodetector element is arranged on the application face.

4. The integrated test element as claimed in claim 1, wherein the at least one indicator substance is merged into the at least one organic layer of the at least one organic electroluminescent component.

5. The integrated test element as claimed in claim 1, wherein the at least one carrier element includes one or more of a needle-shaped, cannula-shaped and lancet-shaped part.

6. The integrated test element as claimed in claim 1, wherein the excitation light emitted by the at least one organic electroluminescent component is at least partially prevented from reaching the at least one photodetector element.

7. The integrated test element as claimed in claim 6, further including one or more of an optical filter element and a light-blocker element.

8. The integrated test element as claimed in claim 1, wherein the at least one reference device includes at least one or both of a reflector and a reference fluorophore.

9. The integrated test element of claim 1, wherein at least one of the organic electroluminescent component and the photodetector element is composed of several individual organic electroluminescent components or photodetector elements, respectively, in particular of at least one matrix of such components.

10. The integrated test element of claim 1, wherein the at least one organic electroluminescent component and the at least one photodetector element are arranged in the same layer plane on the carrier element.

11. The integrated test element as claimed in claim 1, further comprising: an additional barrier layer that at least partially covers the integrated test element, said barrier layer including at least one of the following properties: an impermeability to the at least one indicator substance; an at least partial permeability to the sample; and an action separating the sample at least partially into its constituents.

12. The integrated test element as claimed in claim 1, wherein the at least one indicator substance is chemically bound with the at least one organic layer of the at least one organic electroluminescent component.

13. The integrated test element as claimed in claim 5, wherein the one or more of the needle-shaped, cannula-shaped and lancet-shaped part is configured for at least one of piercing of and insertion into a body tissue.

14. The integrated test element as claimed in claim 8, wherein the at least one reference device includes a paper brightener.

15. The integrated test element as claimed in claim 8, wherein the at least one reference device includes a metal oxide.

16. The integrated test element as claimed in claim 15, wherein the metal oxide includes $TiO_2$.

17. An integrated test element for detecting at least one analyte in a sample, comprising:
a carrier element including at least one organic light-emitting diode (OLED) applied on an application face of the carrier element, the at least one OLED including one or more organic layers positioned between opposite electrodes;
at least one photodetector element; and
at least one indicator substance positioned between the electrodes of the at least one OLED;
wherein the at least one OLED is configured to emit excitation light such that at least some of the excitation light reaches the at least one indicator substance, and the at least one indicator substance is designed to alter at least one optical characteristic when the at least one indicator substance comes into contact with the at least one analyte.

18. An integrated test element for detecting at least one analyte in a sample, comprising:
a carrier element including at least one organic light-emitting diode (OLED) applied on an application face of the carrier element, the at least one OLED including oppositely positioned electrodes and one or more organic layers;

at least one photodetector element; and at least one indicator substance merged or chemically bound into at least one layer of the one or more organic layers of the at least one OLED, the at least one layer being positioned between the electrodes of the at least one OLED;

wherein the at least one OLED is configured to emit excitation light such that at least some of the excitation light reaches the at least one indicator substance, and at least one optical characteristic of the at least one indicator substance is alterable when the at least one indicator substance comes into contact with the at least one analyte.

19. The integrated test element of claim 18, wherein the at least one OLED is further configured such that the at least one indicator substance is surrounded by light-emitting molecules when the at least one OLED emits excitation light.

20. The integrated test element of claim 18, wherein the at least one OLED is further configured such that formation of the excitation light, reaction of the at least one indicator substance with the at least one analyte, and excitation of the at least one indicator substance by the excitation light occurs between the electrodes of the at least one OLED.

21. An integrated test element for detecting at least one analyte in a sample, comprising:

a carrier element including at least one organic light-emitting diode (OLED) applied on an application face of the carrier element, the at least one OLED including one or more organic layers positioned between opposite electrodes;

at least one photodetector element; and at least one indicator substance positioned between the electrodes of the at least one OLED;

wherein the at least one OLED is configured to emit excitation light such that at least some of the excitation light reaches the at least one indicator substance and the at least one indicator substance is surrounded by light-emitting molecules when the at least one OLED emits excitation light, and at least one optical characteristic of the at least one indicator substance is alterable when the at least one indicator substance comes into contact with the at least one analyte.

22. The integrated test element of claim 21, wherein the at least one indicator substance is merged or chemically bound into at least one layer of the one or more organic layers of the at least one OLED, the at least one layer being positioned between the electrodes of the at least one OLED.

23. The integrated test element of claim 21, wherein the at least one OLED is further configured such that formation of the excitation light, reaction of the at least one indicator substance with the at least one analyte, and excitation of the at least one indicator substance by the excitation light occurs between the electrodes of the at least one OLED.

24. An integrated test element for detecting at least one analyte in a sample, comprising:

a carrier element including at least one organic light-emitting diode (OLED) applied on an application face of the carrier element, the at least one OLED including one or more organic layers positioned between opposite electrodes;

at least one photodetector element; and at least one indicator substance;

wherein the at least one OLED is configured such that formation of excitation light, reaction of the at least one indicator substance with the at least one analyte, and excitation of the at least one indicator substance by the excitation light occurs between the electrodes of the at least one OLED, and at least one optical characteristic of the at least one indicator substance is alterable when the at least one indicator substance comes into contact with the at least one analyte.

25. The integrated test element of claim 24, wherein the at least one indicator substance is merged or chemically bound into at least one layer of the one or more organic layers of the at least one OLED, the at least one layer being positioned between the electrodes of the at least one OLED.

26. The integrated test element of claim 24, wherein the at least one OLED is further configured such that the at least one indicator substance is surrounded by light-emitting molecules upon formation of the excitation light.

* * * * *